United States Patent
Ganta et al.

(10) Patent No.: US 11,541,108 B2
(45) Date of Patent: Jan. 3, 2023

(54) TARGETED GENE DISRUPTION METHODS AND IMMUNOGENIC COMPOSITIONS

(71) Applicant: Kansas State University Research Foundation, Manhattan, KS (US)

(72) Inventors: Roman R. Ganta, Manhattan, KS (US); Ying Wang, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 157 days.

(21) Appl. No.: 16/609,097

(22) PCT Filed: Apr. 30, 2018

(86) PCT No.: PCT/US2018/030302
§ 371 (c)(1),
(2) Date: Oct. 28, 2019

(87) PCT Pub. No.: WO2018/201153
PCT Pub. Date: Nov. 1, 2018

(65) Prior Publication Data
US 2020/0188498 A1    Jun. 18, 2020

Related U.S. Application Data

(60) Provisional application No. 62/491,896, filed on Apr. 28, 2017.

(51) Int. Cl.
*A01N 63/00* (2020.01)
*A61K 39/02* (2006.01)
*A61K 39/118* (2006.01)
*C12N 1/20* (2006.01)
*A61K 39/00* (2006.01)

(52) U.S. Cl.
CPC ........ *A61K 39/0233* (2013.01); *A61K 39/118* (2013.01); *C12N 1/20* (2013.01); *A61K 2039/522* (2013.01); *A61K 2039/552* (2013.01)

(58) Field of Classification Search
CPC .............................................. A61K 39/0233
See application file for complete search history.

(56) References Cited

U.S. PATENT DOCUMENTS

2003/0092087 A1* 5/2003 Walker ................... C07K 14/29
435/7.32
2016/0015798 A1 1/2016 Caldwell

FOREIGN PATENT DOCUMENTS

WO    2016118512 A1    7/2016

OTHER PUBLICATIONS

Wang, et al., A genetic system for targeted mutations to disrupt and restore genes in the obligate bacterium, Ehrlichia chaffeensis, Sci Rep, Nov. 17, 2017, vol. 7, pp. 1-13.
Arathy D. S. Nair et al.: Attenuated Mutants of Ehrlichia chaffeensis Induce Protection against Wild-Type Infection Challenge n the Reservoir Host and in an Incidental Host:, Infection and Immunity, vol. 83, No. 7., Jul. 1, 2015, pp. 2827-2835, XP055752661, ISSN: 00199567, DOI: 10.1128/1AI.00487-15.
Chuanmin Cheng et al.: "Targeted and Random Mutagenesis of Ehrilichia chaffeensis for the Indentification of Genes Required for In vivo Infection", Plos Pathogens, vol. 9. No. 2, Feb. 14, 2013, p. e1003171, XP055752668, DOI: 10.137/journal.ppat.1003171.
Konrad E. Mueller et al.: "Gene Deletion by Fluorescence-Reported Allelic Exchange Mutagenesis in Chlamydia trachomatis", MBIO, vol. 7. mp/ 1, Mar. 2, 2016, p. e01817-1,XP055752514, DOI: 10.1128/mBio.01817-15.
Extended European Search Report dated Nov. 23, 2020 in EP18789954 filed Nov. 26, 2019.

\* cited by examiner

*Primary Examiner* — Albert M Navarro
(74) *Attorney, Agent, or Firm* — Tracey S. Truitt; Armstrong Teasdale LLP

(57) ABSTRACT

Targeted disruption of a specific gene and its subsequent restoration in obligate intracellular bacteria remains extremely challenging due to their absolute requirement for residence inside a host cell to replicate. Here, targeted allelic exchange mutations were created to inactivate two genes and then to restore one of the two genes of a rickettsial pathogen, *Ehrlichia chaffeensis*. These methods were then also successfully utilized in *Ehrlichia canis* and *Anaplasma phagocyophilum*. The resultant mutated pathogens are useful in immunogenic compositions for reducing the incidence of or severity of infection with ricksettsial pathogens.

23 Claims, 17 Drawing Sheets
Specification includes a Sequence Listing.

TARGETED GENE DISRUPTION METHODS AND IMMUNOGENIC COMPOSITIONS

The invention was made with government support under grant No. AI070908, awarded by the NIH. The government has certain rights in the invention.

BACKGROUND OF THE INVENTION

Disrupting specific gene function and subsequent restoration of its activity in obligate intracellular bacteria remains extremely challenging due to their absolute requirement for residence inside a host cell to replicate. Here, we created targeted mutations by allelic exchange in two genes and genetically complemented one gene of the rickettsial pathogen *Ehrlichia chaffeensis*. In principle, this approach can be applied to other obligate intracellular bacteria and will enable structure-function analyses routinely done in intracellular bacteria. The method is also applicable in generating attenuated strains of obligate intracellular bacteria, which will be valuable in serving as live vaccine candidates.

Obligate intracellular bacteria (hereafter "obligates") are responsible for causing diseases in millions of people worldwide. They include many pathogenic Gram-negatives of the orders Rickettsiales and Chlamydiales. Lack of an efficient system for targeted mutagenesis in Rickettsiales and Chlamydiales of the genera *Ehrlichia, Anaplasma, Rickettsia, Neorickettssia, Orientia* and *Chlamydia* remains a major impediment in understanding microbial pathogenesis and in defining the functional significance of many bacterial genes. Chlamydiales and Rickettsiales have undergone extreme genome reductions where the majority of genes for each pathogen may be critical for their intracellular growth. Thus, obligate intracellular bacteria depend on their hosts to fill in the deficiencies resulting from genome reductions. Consistent with this hypothesis, prior studies demonstrate that nearly 74-92% of the predicted genes in *Ehrlichia, Anaplasma, Rickettsia, Neorickettsia*, and *Chlamydia* species are transcriptionally active during bacterial replication in the host cells of vertebrates and vectors. Challenges in creating targeted mutations may be attributed to the essential nature of a gene selected for mutagenesis, intracellular replication dependence and the lack of methods to support extracellular growth. Despite the success in generating random mutations using transposon mutagenesis, generating targeted mutations in specific genes of interest followed by complementation is problematic and is also a highly sought-after goal for obligates.

BRIEF SUMMARY OF THE INVENTION

The present disclosure fills this major gap by providing methods to generate at least one stable targeted mutation by allelic exchange in Rickettsiales and Chlamydiales. Advantageously, the disclosure further provides the ability to disrupt or inactivate multiple genes and thereafter restore at least one intact gene by another allelic exchange mutation, resulting in the restored transcription from the inactivated gene from its own promoter. In preferred forms, the disrupted or inactivated genes prevent or at least decrease the ability of the bacteria to replicate in its obligate host while still inducing an immune response specific for the bacteria. Thus, the present disclosure provides attenuated forms of the bacteria that will be useful in immunogenic compositions that induce immune responses that decrease the incidence or severity of at least one clinical sign associated with or caused by Rickettsiales and Chlamydiales when administered prophylactically, and decrease the duration or severity of at least one clinical sign associated with or caused by Rickettsiales and Chlamydiales when administered after infection has already occurred.

"Sequence Identity" as it is known in the art refers to a relationship between two or more polypeptide (poly amino acid) sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or amino acid residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs, which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

Those of skill in the art will understand that the immunogenic composition used herein may incorporate known injectable, physiologically acceptable sterile solutions for preparing a ready-to-use solution for parenteral injection or infusion, aqueous isotonic solutions, such as e.g. saline or corresponding plasma protein solutions, are readily available. In addition, the immunogenic and vaccine compositions of the present disclosure can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In one aspect, the immunogenic composition may also comprise additional elements, antigens, pharmaceutical-acceptable carriers, veterinary-acceptable carriers, adjuvants, preservatives, stabilizers, or combinations thereof.

"Adjuvants" as used herein, can include aluminum hydroxide and aluminum phosphate, saponins, Quil A, cyclic GMP-AMP, montanide gel, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). JohnWiley and Sons, NY, pp 51-94 (1995) and Todd et al., Vaccine 15:564-570 (1997). For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book. A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314, or muramyl dipeptide among many others.

Preferably, the adjuvant is added in an amount of about 100 μg to about 10 mg per dose. Even more preferably, the adjuvant is added in an amount of about 100 μg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

Additionally, the composition can include one or more pharmaceutical-acceptable or veterinary-acceptable carriers. As used herein, "a pharmaceutical-acceptable carrier" or "a veterinary-acceptable carrier" includes any and all solvents, dispersion media, coatings, stabilizing agents, diluents, preservatives, antibacterial and antifungal agents, isotonic agents, adsorption delaying agents, and the like.

Pharmaceutically acceptable vehicle is understood as designating a compound or a combination of compounds entering into a pharmaceutical composition or vaccine which does not provoke secondary reactions and which allows, for example, the facilitation of the administration of the active compound, an increase in its duration of life and/or its efficacy in the body, an increase in its solubility in solution or alternatively an improvement in its conservation. These pharmaceutically acceptable vehicles are well known and will be adapted by the person skilled in the art as a function of the nature and of the mode of administration of the chosen active compound.

For example, the immunogenic composition or vaccine according to the present disclosure may be administered one time or several times, spread out over time in an amount of about 0.1 to 1000 µg per kilogram weight of the animal or human, where values and ranges such as, but not limited to, 0.5 to 800 µg per kilogram weight of the animal or human, 1 to 1000 µg per kilogram weight of the animal or human, 1 to 500 µg per kilogram weight of the animal or human, 1 to 300 µg per kilogram weight of the animal or human, 1 to 200 µg per kilogram weight of the animal or human, 1 to 150 µg per kilogram weight of the animal or human, 1 to 125 µg per kilogram weight of the animal or human, 1 to 100 µg per kilogram weight of the animal or human, 5 µg per kilogram weight of the animal or human, 10 µg per kilogram weight of the animal or human, 15 µg per kilogram weight of the animal or human, 20 µg per kilogram weight of the animal or human, 25 µg per kilogram weight of the animal or human, 30 µg per kilogram weight of the animal or human, 35 µg per kilogram weight of the animal or human, 40 µg per kilogram weight of the animal or human, 45 µg per kilogram weight of the animal or human, 50 µg per kilogram weight of the animal or human, 55 µg per kilogram weight of the animal or human, 60 µg per kilogram weight of the animal or human, 65 µg per kilogram weight of the animal or human, 70 µg per kilogram weight of the animal or human, 75 µg per kilogram weight of the animal or human, 80 µg per kilogram weight of the animal or human, 85 µg per kilogram weight of the animal or human, 90 µg per kilogram weight of the animal or human, 95 µg per kilogram weight of the animal or human, 100 µg per kilogram weight of the animal or human, 125 µg per kilogram weight of the animal or human, 150 µg per kilogram weight of the animal or human, 200 µg per kilogram weight of the animal or human, 250 µg per kilogram weight of the animal or human, 300 µg per kilogram weight of the animal or human, 400 µg per kilogram weight of the animal or human, 500 µg per kilogram weight of the animal or human, 600 µg per kilogram weight of the animal or human, 700 µg per kilogram weight of the animal or human, 800 µg per kilogram weight of the animal or human, 900 µg per kilogram weight of the animal or human, and 1000 µg per kilogram weight of the animal or human are envisioned. In other preferred forms, the above amounts are also provided without reference to the weight of the animal or human.

According to the present disclosure, the immunogenic composition or vaccine may include at least one further pathogen other than *E. chaffeensis*, making it a combination vaccine or immunogenic composition. In such an embodiment, an effective amount of a vaccine or immunogenic composition administered provides effective protection including a reduction in the severity or incidence of clinical signs of infection up to and including immunity against infections caused by Rickettsiale or Chlamydiale bacteria and at least one further disease-causing organism. The further pathogen is preferably selected from the group consisting of: *Actinobacillus pleuropneumonia*; Adenovirus; Alphavirus such as Eastern equine encephalomyelitis viruses; *Bordetella bronchiseptica; Brachyspira* spp., preferably *B. hyodyentheriae; B. piosicoli, Brucella suis*, preferably biovars 1, 2, and 3; Classical swine fever virus; *Clostridium* spp., preferably *Cl. difficile, Cl. perfringens* types A, B, and C, *Cl. novyi, Cl. septicum, Cl. tetani*; Coronavirus, preferably Porcine Respiratory Corona virus; *Eperythrozoonosis suis; Erysipelothrix rhusiopathiae; Escherichia coli; Haemophilus parasuis*, preferably subtypes 1, 7 and 14: Hemagglutinating encephalomyelitis virus; Japanese Encephalitis Virus; *Lawsonia intracellularis; Leptospira* spp.; preferably *Leptospira australis; Leptospira canicola; Leptospira grippotyphosa; Leptospira icterohaemorrhagicae*; and *Leptospira interrogans; Leptospira pomona; Leptospira tarassovi; Mycobacterium* spp. preferably *M. avium; M. intracellulare*; and *M. bovis; Mycoplasma hyopneumoniae* (*M. hyo*); *Pasteurella multocida*; Porcine cytomegalovirus; Porcine Parvovirus; Porcine Reproductive and Respiratory Syndrome (PRRS) Virus; Porcine circovirus, Pseudorabies virus; Rotavirus; *Salmonella* spp.; preferably *S. thyhimurium*; and *S. choleraesuis; Staph. hyicus; Staphylococcus* spp., *Streptococcus* spp., preferably *Strep. suis*; Swine herpes virus; Swine Influenza Virus; Swine pox virus; Swine pox virus; Vesicular stomatitis virus; Virus of vesicular exanthema of swine; *Leptospira Hardjo; Mycoplasma hyosynoviae*; Poliovirus; Rhinovirus; hepatitis A virus; foot-and-mouth disease virus (FMDV); swine vesicular disease (SVDV), and combinations thereof.

The immunogenic compositions can further include one or more other immunomodulatory agents such as, e. g., interleukins, interferons, or other cytokines.

The immunogenic compositions can also include Gentamicin and Merthiolate.

While the amounts and concentrations of adjuvants and additives useful in the context of the present invention can readily be determined by the skilled artisan, the present invention contemplates compositions comprising from about 50 μg to about 2000 μg of adjuvant. Thus, the immunogenic composition as used herein also refers to a composition that comprises from about 1 ug/ml to about 60 μg/ml of antibiotics or immunomodulatory agents, and more preferably less than about 30 μg/ml of antibiotics or immunomodulatory agents.

According to a further aspect, at least one further administration of at least one dose of the immunogenic composition as described above is given to a subject in need thereof, wherein the second or any further administration is given at least 7 days beyond the initial or any former administrations. Preferably, the immunogenic composition is administered with an immune stimulant. Preferably, said immune stimulant is given at least twice. Preferably, at least 3 days, more preferably at least 5 days, even more preferably at least 7 days are in between the first and the second or any further administration of the immune stimulant. Preferably, the immune stimulant is given at least 10 days, preferably 15 days, even more preferably 20, even more preferably at least 22 days beyond the initial administration of the immunogenic composition provided herein. A preferred immune stimulant is, for example, keyhole limpet hemocyanin (KLH), preferably emulsified with incomplete Freund's adjuvant (KLH/ICFA). However, it is herewith understood, that any other immune stimulant known to a person skilled in the art can also be used. The term "immune stimulant" as used herein, means any agent or composition that can trigger the immune response, preferably without initiating or increasing a specific immune response, for example the immune response against a specific pathogen. It is further instructed to administer the immune stimulant in a suitable dose.

In further aspect, the present disclosure provides methods for generating at least one stable targeted mutation by allelic exchange for the genera *Ehrlichia, Anaplasma, Neorickettsia, Rickettsia, Orientia* and *Chlamydia*.

In a still further aspect of the present disclosure, Rickettsiales and Chlamydiales mutated using the disclosed methods are useful in immunogenic compositions against Rickettsiale and Chlamydiale pathogens. In preferred forms, such immunogenic compositions are effective at reducing the incidence or severity of at least one clinical sign of infection caused by or associated with infection by Rickettsiale and Chlamydiale pathogens. In some preferred forms, such compositions are administered prophylactically such that clinical signs are reduced in incidence and/or severity. In particularly preferred forms, the clinical signs are prevented in animals receiving such compositions prior to being infected or challenged with Rickettsiale and/or Chlamydiale pathogens. In other forms, such compositions are administered after infection by Rickettsiale and/or Chlamydiale pathogens has already occurred. In such situations, the clinical signs associated with or caused by the infections are reduced in incidence, severity, and/or longevity.

In a further aspect, the stable targeted mutation disrupts the function of at least one gene.

In yet a further aspect, the function of a gene that has been disrupted can be restored.

In one aspect of the present disclosure, stable targeted mutations were made in *E. chaffeensis* where two genes were disrupted and subsequently had function restored from one gene. These same methods were also successfully used in *Ehrlichia* species including *Ehrlichia canis* (*E. canis*) and *Anaplasma* species including *Anaplasma phagocyophilum* (*A. phagocyophilum*).

In another aspect, the present disclosure provides a method of targeted gene disruption or mutation in *Ehrlichia, Anaplasma, Rickettsia, Neorickettsia, Orientia* and/or *Chlamydia* species to generate attenuated organisms of the bacteria, which will be valuable in inducing effective host immune responses to confer protection against the virulent diseases caused by those same species.

In yet a further aspect, a method for eliciting an immune response in a human or animal is provided, where the steps include administration of an immunogenic composition or vaccine disclosed herein to an animal or human in need thereof. Additionally, a method for reducing the incidence and/or severity of at least one or more clinical signs associated with or caused by infection by a pathogen from the genera *Ehrlichia, Anaplasma, Neorickettsia, Rickettsia, Orientia* and/or *Chlamydia* is provided. In some forms, the infection is caused by or associated with *E. chaffeensis, E. canis, A. marginale, A. platys*, and/or *A. phagocyophilum* and the immunogenic composition or vaccine comprises at least one of those species wherein the targeted gene disruption or mutation is performed on such a species. Such a method generally comprises the step of administering the immunogenic composition to an animal in need thereof to elicit an immune response against infection and subsequent exhibition of clinical signs in animals infected or challenged by a species of the genera *Ehrlichia, Anaplasma, Neorickettsia, Rickettsia, Orientia* and *Chlamydia* after administration of the immunogenic composition. In some forms, the immunogenic composition includes a modified live species of *Ehrlichia, Anaplasma, Neorickettsia, Rickettsia, Orientia*, or *Chlamydia.*

In one aspect, the immunogenic composition includes *E. chaffeensis, E. canis, A. phagocyophilum*, or *A. marginale* that has undergone the targeted mutagenesis described herein. When *E. chaffeensis* is the mutated species, the immunogenic composition preferably includes an attenuated *E. chaffeensis* bacteria that includes a mutation that inactivates the bacteria and interferes with its ability to replicate. In some preferred forms, the mutation is an insertion or deletion. In some forms, the insertion or deletion anywhere within a gene selected from the group consisting of Ech_0379 or Ech_0660 gene, resulting in the inactivation of gene function. In some forms, the genome of the *E. chaffeensis* includes a sequence having at least 70%, at least 75%, at least 80%, at least 85%, at least 90%, or at least 95, 96, 97, 98, 99, or even 100% sequence identity to Ech_0660 (SEQ ID No. 35). Preferably the sequence comparison is in comparison to a non-mutated version of the same region of the *E. chaffeensis* genome. When *E. canis* is the mutated species, the immunogenic composition preferably includes an attenuated *E. canis* bacteria that includes a mutation that inactivates the bacterial gene and interferes with its ability to replicate. In some preferred forms, the mutation is an insertion or deletion. In some forms, the insertion or deletion is in the Ecaj_0381 gene anywhere within the gene resulting in the gene function inactivation. In some forms, the genome of the *E. canis* includes a sequence having at least 70%, at least 75%, at least 80%, at least 85%, at least 90%, or at least 95, 96, 97, 98, 99, or even 100% sequence identity to SEQ ID No. 54. Preferably the sequence comparison is in comparison to a non-mutated version of the same region of the *E. canis* genome. When *A. phagocytophilum* is the mutated species, the immunogenic composition preferably includes an attenuated *A. phagocytophilum* bacteria that includes a mutation that inactivates the bacteria and interferes with its ability to replicate. In some preferred forms, the mutation is an insertion or deletion. In some forms, the insertion or deletion is in the APH_0634 gene anywhere within the gene resulting in the gene function inactivation. In some forms, the genome of the *A. phagocytophilum* APH_0634 gene includes a sequence having at least 70%, at least 75%, at least 80%, at least 85%, at least 90%, or at least 95, 96, 97, 98, 99, or even 100% sequence identity to SEQ ID No. 55. Preferably the sequence comparison is in comparison to a non-mutated version of the same region of the *A. phagocytophilum* genome.

The immunogenic composition or vaccine and methods provided in this disclosure are not limited to *E. chaffeensis, E. canis*, or *A. phygocytophilum*, but may also include any member of the orders Rickettsiales or Chlamydiales, including but not limited to the families of Pelagibacterales, Pelagibacteraceae (including subgroups Ib, II, IIIa, IIIb, IV, and V), Pelagibacter, Proro-mitochondira, Anaplasmataceae, species of the genera *Ehrlichia, Anaplasma, Wolbachia, Neorickettsia*; Midichloriaceae, Midichloria, Rickettsiaceae, and *Rickettsia* species. Further, the immunogenic composition or vaccine may also include, but is not limited to, *E. ruminantium, E. canis, A. marginale, A. platys, E. muris* and combinations thereof.

In a further aspect of the present disclosure, the immunogenic composition comprises a homolog of the *E. chaffeensis* ECH_0660 gene that has been mutated using the methods provided herein. In preferred forms, the homolog is selected from the group consisting of the genera *Ehrlichia, Anaplasma, Rickettsia, Neorickettsia, Orientia* and *Chlamydia*. In other preferred forms, the gene homolog is Ecaj_0381 of *E. canis*, preferably having at least 70%, 75%, 80%, 85%, 90%, and more preferably at least 92%, still more preferably at least 94%, even more preferably at least 95, 96, 97, 98, 99, or even 100% sequence homology with GenBank #CP000107.1. In other preferred forms, the gene homolog is Erum_3930 of *E. ruminatium*, preferably having at least 70%, 75%, 80%, 85%, 90%, and more preferably at least 92%, still more preferably at least 94%, even more preferably at least 95, 96, 97, 98, 99, or even 100% sequence homology with GenBank #CR767821.1. In other preferred forms, the gene homolog is APH_0634 of *Anaplasma phagocytophilum*, preferably having at least 70%, 75%, 80%, 85%, 90%, and more preferably at least 92%, still more preferably at least 94%, even more preferably at least 95, 96, 97, 98, 99, or even 100% sequence homology with GenBank #CP000235.1. In other preferred forms, the gene homolog is AMH_581 of *Anaplasma marginale*, preferably having at least 70%, 75%, 80%, 85%, 90%, and more preferably at least 92%, still more preferably at least 94%, even more preferably at least 95, 96, 97, 98, 99, or even 100% sequence homology with GenBank #CP000030.1. In other preferred forms, the gene homolog is EMUR_02070 of *Ehrlichia muris* AS145, preferably having at least 70%, 75%, 80%, 85%, 90%, and more preferably at least 92%, still more preferably at least 94%, even more preferably at least 95, 96, 97, 98, 99, or even 100% sequence homology with GenBank #CP006917.1.

The immunogenic composition according to the disclosure may be administered intravenously, intramuscularly, intranasally, intradermally, intratracheally, intravaginally, intravenously, intravascularly, intraarterially, intraperitoneally, orally, intrathecally, or by direct injection into any target tissue. Depending on the desired duration and effectiveness of the treatment, the immunogenic compositions according to the disclosure may be administered once or several times, also intermittently, for instance on a daily basis for several days, weeks or months and in different dosages.

In another aspect, immunogenic composition of the present disclosure is administered to an animal in need thereof at least two weeks of age. More preferably, the animal is between 2 weeks and 1 year of age, still more preferably between 3 weeks and 6 months of age. Of course, other ages and ranges are contemplated such as 4, 5, 6, 7, 8, 9, 10, 11, 12, 13, 14, 15, 16, 17, 18, 19, and 20 weeks or more. Alternatively, the immunogenic composition is administered at least 2 weeks prior to exposure to a Rickettsiale or Chlamydiale bacteria.

In some forms, the immunogenic composition is administered after infection by the Rickettsiale or Chlamydiale bacteria. In such situations, the administration reduces the duration or severity of clinical signs associated with or caused by the infection.

In another aspect, the present disclosure provides an immunogenic composition comprising a Rickettsiale or Chlamydiale bacteria having a targeted allelic exchange mutation therein and a component selected from the group consisting of a veterinary-acceptable carrier, a pharmaceutical-acceptable carrier, an adjuvant, a preservative, a buffer, an antibiotic, cell culture supernatant, an immunomodulatory agent and any combination thereof. In some forms, the immunogenic composition the Rickettsiale or Chlamydiale bacteria is selected from the group consisting of species of *Ehrlichia, Anaplasma, Neorickettsia, Rickettsia, Orientia* and *Chlamydia*. In some forms, the *Ehrlichia* species bacteria are selected from the group consisting of *Ehrlichia chaffeensis, Ehrlichia canis, Ehrlichia ruminatium, Ehrlichia muris* and *Ehrlichia muris* like agent. In some forms, the *Anaplasma* bacteria species are selected from the group consisting of *Anaplasma phagocytophilum, Anaplasma platys*, and *Anaplasma marginale*. In some forms, the targeted allelic exchange mutation inactivates a gene. In some forms, the inactivation results from an insertion or deletion. In some forms, the inactivation results in a decreased ability of the bacteria to replicate. In some forms, the targeted allelic exchange mutation is in Ech_0230, Ech_0379, or Ech_0660 in *Ehrlichia chaffeensis*. In some forms, the targeted allelic exchange mutation is in Ecaj_0381 in *Ehrlichia canis*. In some forms, the targeted allelic exchange mutation is in APH_0634 in *Anaplasma phagocytophilum*.

In another aspect, the present disclosure provides a method of reducing the incidence of or severity of at least one clinical sign caused by a Rickettsiale or Chlamydiale bacteria comprising the step of administering an immunogenic composition comprising a Rickettsiale or Chlamydiale bacteria having a targeted allelic exchange mutation therein and a component selected from the group consisting of a veterinary-acceptable carrier, a pharmaceutical-acceptable carrier, an adjuvant, a preservative, a buffer, an antibiotic, cell culture supernatant, an immunomodulatory agent. In some forms, the administering step is selected from the group consisting of intramuscularly, intranasally, intradermally, intratracheally, intravaginally, intravenously, intravascularly, intraarterially, intraperitoneally, orally, intrathecally, or by direct injection into target tissues. In some forms, the administration of the immunogenic composition can be termed a first administration and this first administration is followed by a second administration. In some forms, the second administration is at least 7 days after the first administration. In preferred forms, the reduction in incidence is in a group of animals that have received an administration of the immunogenic composition and at least 10% is in comparison to a group of animals that have not received an administration of the immunogenic composition. In preferred forms, the reduction in severity is assessed in a single animal that has received an administration of the immunogenic composition and is in comparison to an animal that has not received the immunogenic composition. In preferred forms, this reduction in severity is at least 10% when comparing an animal that has received the composition with an animal that has not received the immunogenic composition and that has been subsequently infected or challenged by a Rickettsiale or Chlamydiale bacteria. In some forms, the reduction in severity in a group of animals that have received the immunogenic composition is at least 10% in comparison to a group of animals that have not received an administration of the immunogenic composition. In some forms, the Rickettsiale or Chlamydiale bacteria is selected from the group consisting of *Ehrlichia, Anaplasma, Rickettsia, Neorickettsia, Orientia* and *Chlamydia*. In some forms, the *Ehrlichia* bacteria are selected from the group consisting of *Ehrlichia chaffeensis, Ehrlichia ruminatium, Ehrlichia muris*, and *Ehrlichia canis*. In some forms, the *Anaplasma* bacteria are selected from the group consisting of *Anaplasma phagocytophilum*, *Anaplasma platys*, and *Anaplasma marginale*. In some forms, the targeted allelic exchange mutation inactivates a gene. In some forms, the inactivation results from an insertion or deletion. In some forms, the inactivation results in a decreased ability of the bacteria to replicate. In some forms, the targeted allelic exchange mutation is in Ech_0230, Ech_0379, or Ech_0660 in *Ehrlichia chaffeensis*. In some forms, the targeted allelic exchange mutation is in Ecaj_0381 in *Ehrlichia canis*. In some forms, the targeted allelic exchange mutation is in APH_0634 in *Anaplasma phagocytophilum*. In some forms, the component is an adjuvant selected from the group consisting of a saponin, cyclic GMP-AMP, montanide gel, or any combination thereof.

DETAILED DESCRIPTION OF THE INVENTION

Figure 1:
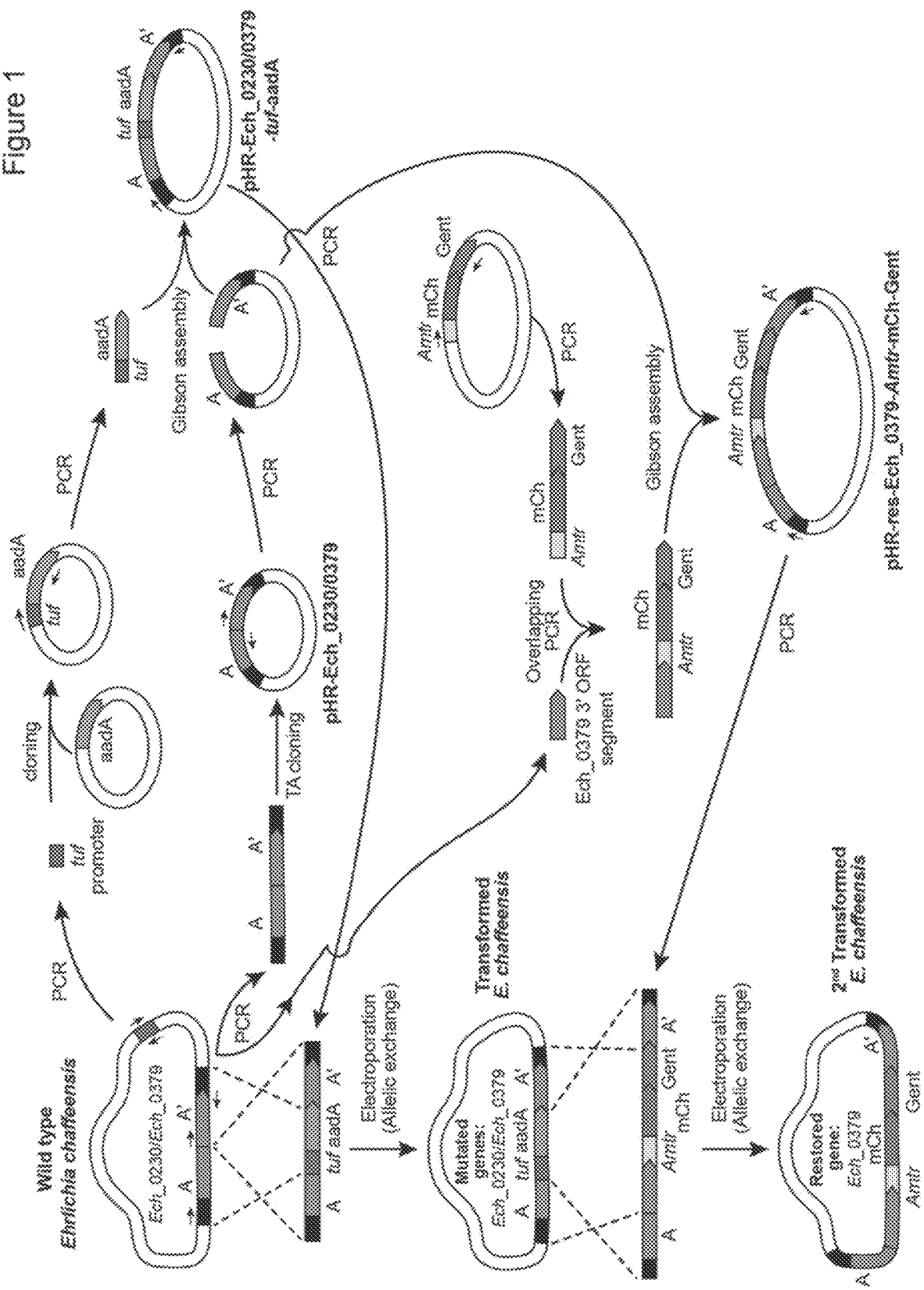
FIG. 1 is an illustration outlining the schematic representation of the strategies employed for creating targeted allelic exchange mutations in *E. chaffeensis* to inactivate genes Ech_0230 and Ech_0379 and to restore the inactivated gene function of Ech_0379, wherein A and A' refer to 5' and 3' homology arms.

The present disclosure provides for a method of providing stable, immunogenic bacteria capable of producing an immunogenic response in a host. The method preferably comprises the steps of a targeted disruption in the genome of the bacterial strain and then performing an allelic exchange.

The present disclosure provides for an immunogenic composition or vaccine that comprises administration of the immunogenic bacteria disclosed herein. The immunogenic bacteria for use in the immunogenic composition or vaccine may be killed, modified killed, modified live, a recombinant protein, a protein, and combinations thereof. In preferred forms, the modified live immunogenic bacteria are attenuated.

A method for preventing or treating at least one of rickettsioses, ehrlichiosis, Rocky Mountain Spotted Fever, human monocyte ehrlichiosis, granulocytic anaplasmosis, and/or anaplasmosis is provided. The steps of the method generally include administration of the immunogenic composition or vaccine disclosed herein to a human or animal in need thereof.

A method for reducing the incidence or severity of clinical symptoms associated with at least one of rickettsioses, ehrlichiosis, Rocky Mountain Spotted Fever, human monocyte ehrlichiosis, granulocytic anaplasmosis, and/or anaplasmosis is provided, where the steps generally include administration of the immunogenic composition or vaccine disclosed herein to a human or animal in need thereof. The clinical symptoms generally include, but are not limited to, fever, headache, chills, malaise, muscle pain, abdominal pain, nausea, vomiting, diarrhea, confusion, conjunctival injection (red eyes), rash, and combinations thereof. Preferably the clinical symptoms associated with at least one of rickettsioses, ehrlichiosis, Rocky Mountain Spotted Fever, human monocyte ehrlichiosis, granulocytic anaplasmosis, and/or anaplasmosis are reduced in frequency and/or severity by at least 10%, at least 20%, at least 30%, at least 40%, at least 50%, at least 60%, at least 70%, at least 80%, at least 90% or reduced by 100%. This is in comparison to an animal or human not receiving the immunogenic composition or vaccine of the present disclosure. Comparisons to groups of animals or humans is also contemplated herein.

The recipient of the product and method of the present disclosure may be a human or an animal. The animal is preferably selected from, but not limited to, porcine, pigs, cattle, goats, horses, dogs, deer, coyote, cats, poultry, and other related wild and domestic animals. In a preferred embodiment, the recipient is a human, a dog, a cow or cattle, a horse, or a pig.

Modified or modified live nucleotide sequence will be understood as meaning any nucleotide sequence obtained by mutagenesis according to techniques well known to the person skilled in the art, and containing modifications with respect to the normal sequences according to the disclosure, for example mutations in the regulatory and/or promoter sequences of polypeptide expression, especially leading to a modification of the rate of expression of said polypeptide or to a modulation of the replicative cycle.

Nucleotide, polynucleotide or nucleic acid sequence will be understood according to the present disclosure as meaning both a double-stranded or single-stranded DNA in the monomeric and dimeric (so-called in tandem) forms and the transcription products of said DNAs.

It must be understood that the present disclosure does not relate to the genomic nucleotide sequences taken in their natural environment, that is to say, in the natural state. It concerns sequences for which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning and subcloning, it being possible for the sequences of the disclosure to be carried by vectors. Further, the sequences have been altered from what is found in nature to include mutations induced through site-directed mutagenesis or other attenuation techniques, such as serial passaging, further demonstrating that the sequences are made by the hand of man and not found in nature.

The attenuated modified live vaccine or immunogenic composition of the present invention does not contain a nucleotide or amino acid sequence found in nature, as it has been constructed by the hand of man. Therefore, the immunogenic composition or vaccine of the present invention is markedly different from what is found in nature. Similar to Example 5 for the Nature-Based Product Examples of eligible subject matter under 35 U.S.C. 101 issued by the US Patent Office in 2014, the immunogenic composition or vaccine of the present invention is like claim 2 of that example because the immunogenic composition or vaccine gene has additional elements, such as the mutations within the sequence or inactivation of the virus that provides it with a functionally different characteristic than, for example, naturally occurring *E. chaffeensis*.

Figure 5A:
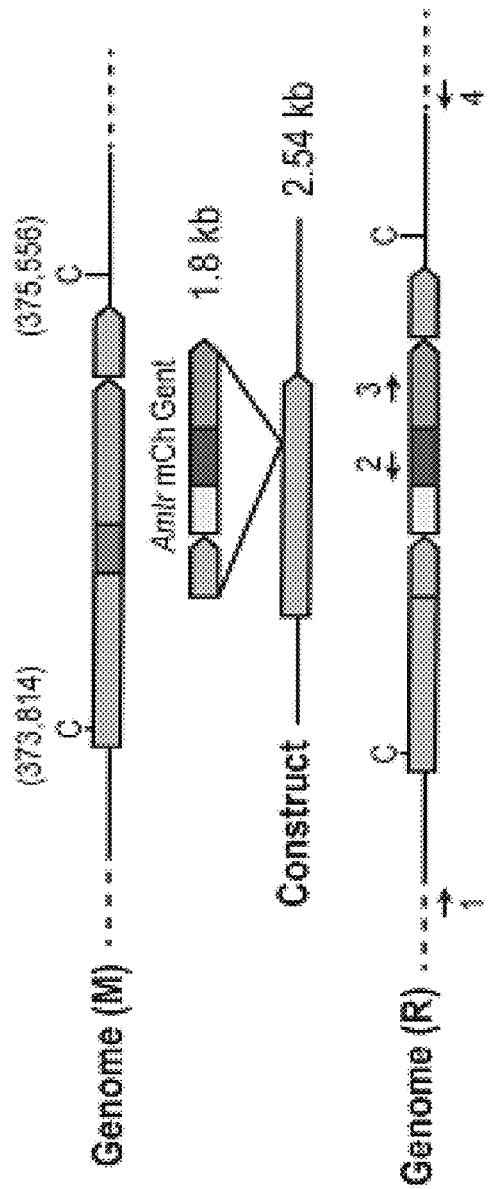
FIG. 5A illustrates targeted allelic exchange mutagenesis to restore the Ech_0379 gene similar to FIG. 3 except that the illustration depicting the genomic segment at the top portion of the panel represents the genome from Ech_0379 mutant.
Figure 5B:
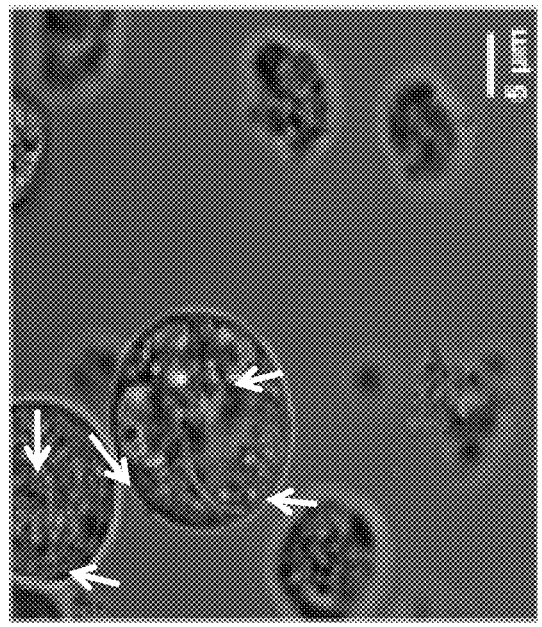
FIG. 5B illustrates the Ech_0379 gene restoration mutant culture expressing mCherry. The restored mutant organisms cultured in ISE6 cells were assessed for the mCherry expression by confocal microscopy using 40× magnification lens wherein the mCherry expression was exhibited at the arrow.
Figure 5C:
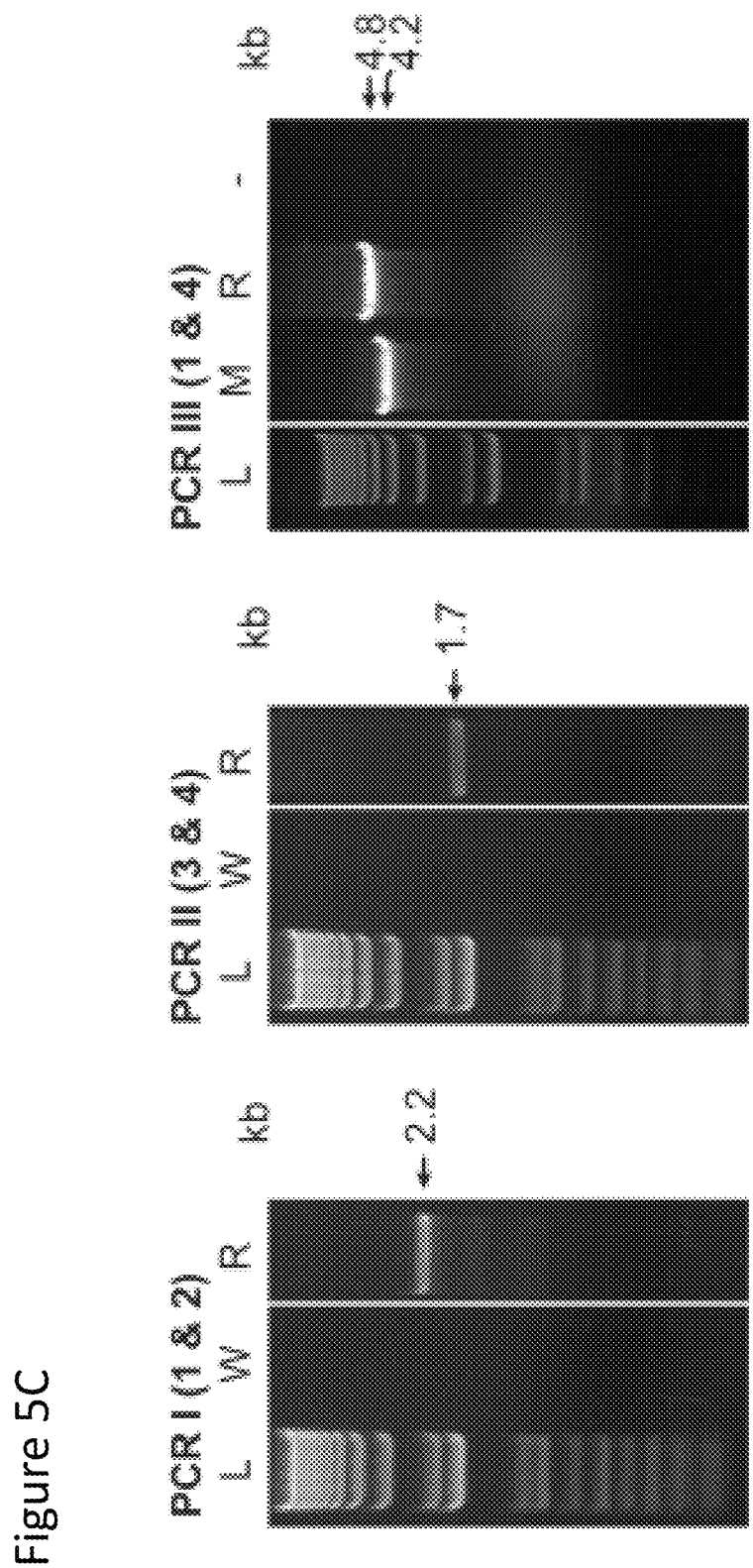
FIG. 5C is a picture showing amplicons resolved following three different PCRs using primers targeting to the genomic regions upstream and downstream to the allelic insertion (primers identified as 1 and 4) and to the inserted DNA (primers; 2 and 3). (L, 1 kb plus molecular weight DNA markers; Wild Type (W), PCR with wild type genomic DNA as the template; Mutant (M), PCR with mutant genomic DNA as the template.
Figure 5D:
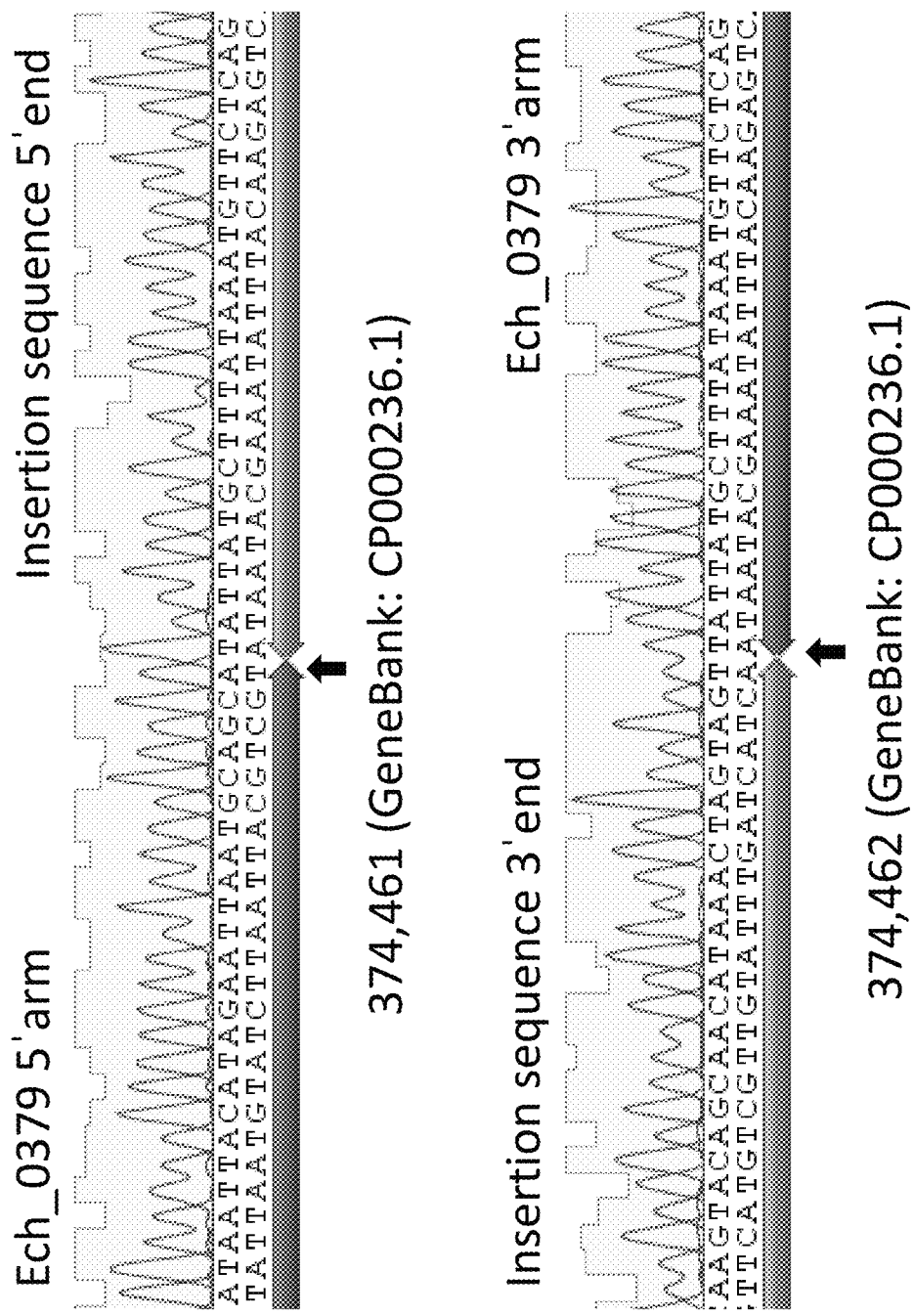
FIG. 5D is a picture showing targeted allelic exchange mutagenesis to restore the Ech_0379 gene. This figure is similar to FIG. 3C except the restriction enzyme and probe used for the Southern blot experiment (shown in FIG. 5E) were Cla I and a DNA segment representing Ech_0379 gene, respectively. Additionally in the top panel of FIG. 5D, the sequence on top is SEQ ID NO. 46 and the sequence on the bottom is SEQ ID NO. 52. In the bottom panel, the top sequence is SEQ ID NO. 47 and the bottom sequence is SEQ ID NO. 53.
Figure 5E:
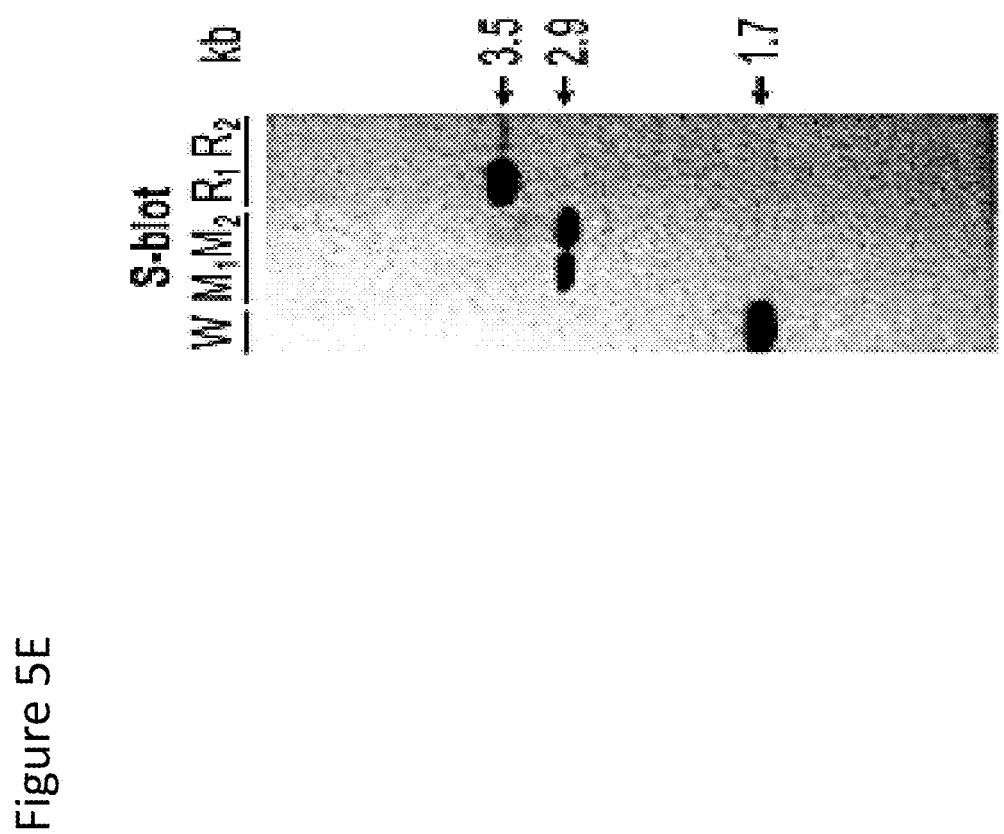
FIG. 5E is a picture of a Southern blot analysis of genomic DNAs (W and M) digested with ClaI (C) or EcoRI (E). The blot analysis was performed with aadA gene segment as the probe illustrates. Lanes $M_1$ and $M_2$ represent data from genomic DNA recovered from the *E. chaffeensis* Ech_0379 mutant culture recovered from DH82 and ISE6 culture, respectively. Similarly, $R_1$ and $R_2$ represent data from genomic DNA recovered from the *E. chaffeensis* Ech_0379 reverted mutant culture recovered from DH82 and ISE6 culture, respectively.
Figure 6B:
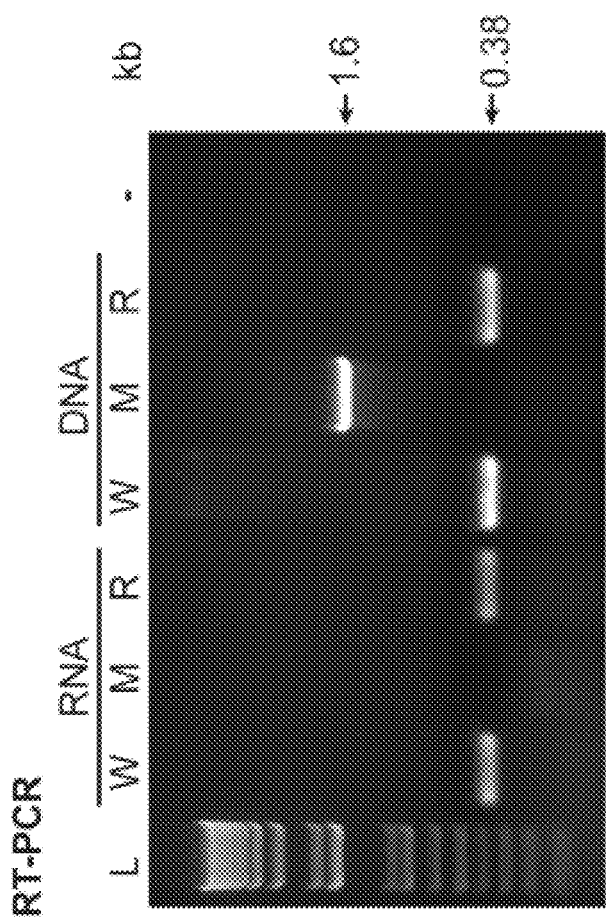
FIG. 6B is similar to FIG. 6A, except that the analysis was performed using RNA recovered from Ech_0379 disruption (M) and restoration (R) mutant organisms. Positive controls for this experiments included genomic DNAs as the templates from W, M and R. (0.38 kb amplicons are expected for DNA templates in PCRs of W and R and 1.6 kb product is expected for M DNA as the template.
Figure 6A:
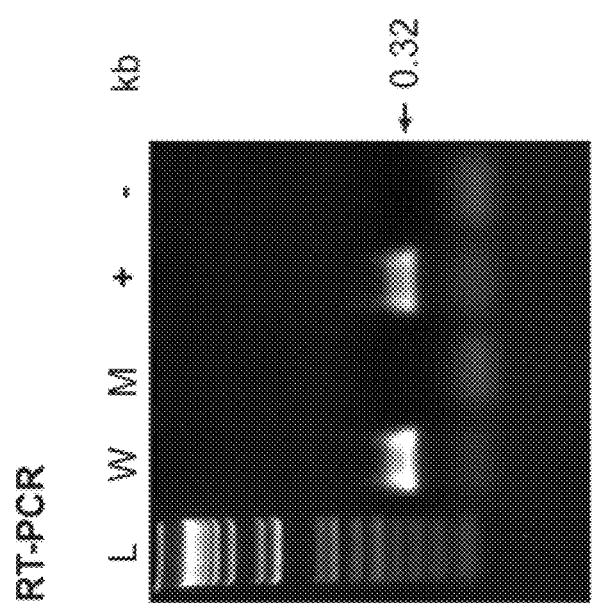
FIG. 6A illustrates transcriptional analysis of RNA recovered from wild type and allelic exchange mutant *E. chaffeensis* organisms assessed by RT-PCR. RT-PCR products from wild type (W) and Ech_0230 mutant (M) organisms were resolved (L, 1 kb plus molecular weight DNA markers resolved; +, genomic DNA from wild type *E. chaffeensis* was used as the template; −, negative control reaction with no template added).
Figure 6C:
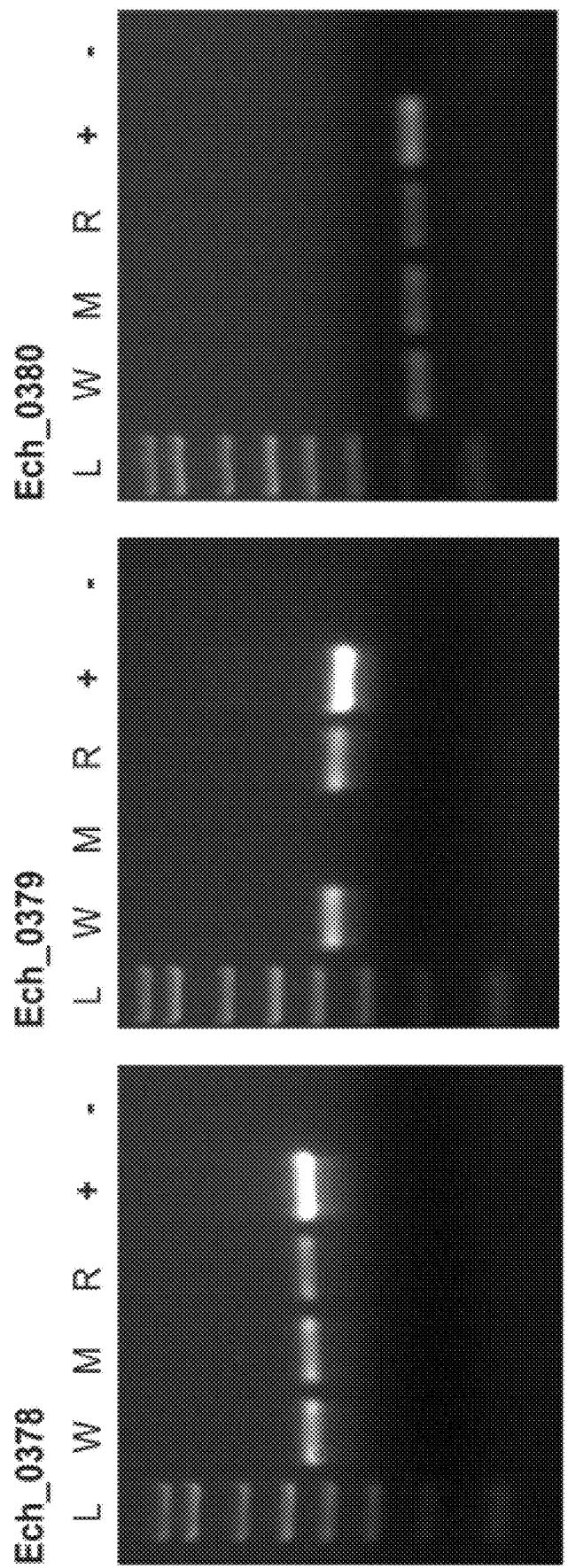
FIG. 6C illustrates transcriptional analysis of RNA recovered from wild type and allelic exchange mutant *E. chaffeensis* organisms assessed by RT-PCR. Mutations to inactivate and restore the gene activity in Ech_0379 did not alter the gene expression from its neighboring genes. Semi-quantitative RT-PCR assays were performed at 30, 35 and 40 PCR cycles for Ech_0378, Ech_0379 and Ech_0380 for wild type, gene inactivation and gene rescue mutant organisms and the data for 35 cycles were presented. W, M and R had similar quantities of amplicons for Ech_0378 and Ech_0380; Ech_0379 amplicons were also similar for W and R, while absent for M.
Figure 7:
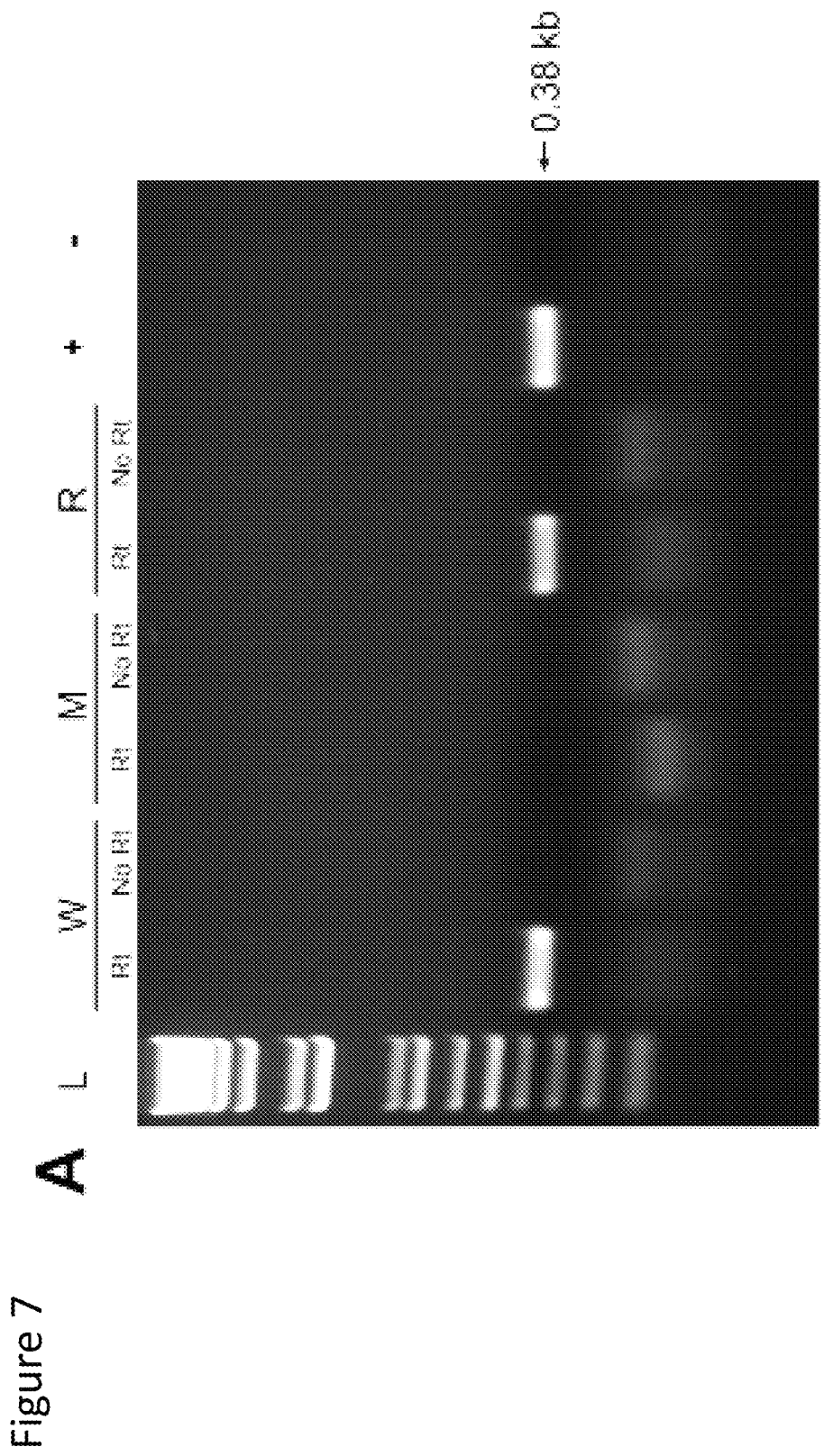
FIG. 7 illustrates phenotypic characterization of Ech_0379 gene in antiporter deficient *E. coli* strain EP432. RT-PCR analysis targeting to Ech_0379 transcripts in EP432 was performed Phenotypic characterization of Ech_0379 gene in antiporter deficient *E. coli* strain EP432.

About 1 kb of *E. chaffeensis* genomic DNA segments upstream and downstream of the previously defined random insertion mutation sites of the Ech_0230 and Ech_0379 gene were obtained by PCR and cloned into a plasmid vector. The promoter segment of *E. chaffeensis* elongation factor Tu gene, Tuf-2, (Ech_0407) was similarly cloned in front of the aadA gene coding sequence into a separate plasmid (aadA gene confers resistance to spectinomycin and streptomycin). Tuf-2 gene promoter (tuf) was chosen for aadA protein expression because it drives the expression of a highly conserved and constitutively expressed protein, Tu that is necessary for the polypeptide elongation process in the protein translation machinery. Further, our bioinformatics analysis and transcription mapping by primer extension experiment suggested that it is a strong promoter responsible for transcribing genes, most of which encode for 30S and 50S ribosomal proteins, and having multiple transcription start sites (not shown). The aadA gene was chosen as it works well in conferring antibiotic resistance in *E. chaffeensis* and in *Anaplasma* species. The tuf-aadA segment was engineered into the homologous recombination constructs of Ech_0230 and Ech_0379 (pHR-Ech_0230-tuf-aadA and pHR-Ech_0379-tuf-aadA, respectively). Linear DNA fragments from the constructs containing the 5' and 3' homology arms of the genes separated by the tuf-aadA segment were generated by PCR for use in creating targeted mutations. To create a rescue mutagenesis template in reversing the targeted gene mutation within the Ech_0379 gene, 0.5 kb fragment downstream from the mutation site of the gene was obtained by PCR from *E. chaffeensis* genome and it was engineered into the pHR-Ech_0379-tuf-aadA construct to generate a modified construct; pHR-res-Ech_0379-Amtr-mCh-Gent containing the entire Ech_0379 gene ORF at the 5' end followed by the presence of the Amtr promoter, the ORFs of mCherry and the gentamicin resistance cassettes (Gent) (Amtr-mCh-Gent) and a 1 kb genomic segment containing the 3' portion of the Ech_0379 gene. Gent was codon optimized for efficient translation in *E. chaffeensis*. Linear fragments from the rescue construct were then prepared which contained the 5'homology arm beginning with the Ech_0379 gene followed by Amtr-mCh-Gent segment and the 3' end genomic segment downstream to the Ech_0379 insertion to serve as the 3' homology arm. Linear DNA fragments to disrupt Ech_0230 or Ech_0379 genes were electroporated into host cell-free wild type *E. chaffeensis* organisms recovered from ISE6 tick cells and then allowed to re-infect ISE6 tick cells. The mutants were selected for their ability to grow in the medium containing spectinomycin and streptomycin for several weeks and then allowed to infect macrophage cell line, DH82, for continued growth for several months. For rescue mutation experiment, linear DNA fragments of the Ech_0379 gene restoration template were similarly electroporated into *E. chaffeensis* organisms containing mutation in the Ech_0379 gene. *E. chaffeensis* cultures with Ech_0379 gene restored were then selected by their ability to grow in the medium containing gentamicin. Following the recovery of *E. chaffeensis* cultures growing in the media containing antibiotics, targeted gene inactivations in Ech_0230 or Ech_0379 were confirmed by two insertion specific PCR assays targeting 1) to the genomic region 5' to the allelic exchange site and to the insertion specific DNA, and 2) to the insertion DNA and to the 3' of the allelic exchange site on the genome. Clonal purity was then confirmed by another PCR assay targeting the genomic regions upstream and downstream of the allelic exchange insertion sites. The integrity of the PCR products was confirmed by PCR-DNA sequence analysis. For Ech_0379 gene restoration mutant generation was also assessed for the mCherry protein expression by fluorescence microscopy (FIG. 5B). The presence of mutations in the *E. chaffeensis* genome was also validated by Southern blot analysis for both the gene disruption mutations and gene restoration mutation. RT-PCR analysis revealed that the Ech_0230 and Ech_0379 transcripts were present in wild type *E. chaffeensis* and were absent in the gene disruption mutant organisms. The complemented mutant strain tested positive for the Ech_0379 transcript similar to wild type *E. chaffeensis*. Further, we tested if the allelic exchange mutations to inactivate and restore gene activity in Ech_0379 can cause polar effects in altering the gene expression from its neighboring genes. The analysis was carried out by semi-quantitative RT-PCR assays where three sets of PCR cycles were used; 30, 35 and 40. Independent of the numbers of PCR cycles performed, RT-PCR products were similar for Ech_0378 and Ech_0380 for wild type, gene inactivation mutant and gene rescue mutant, and Ech_0379 RT-PCR products were absent only in the gene inactivation mutant, while appeared similar for wild type and gene rescue mutant (FIG. 6C). There was no evidence to support the presence of off-target insertions developed during all the three mutational experiments. The Ech_0379 gene open reading frame is completely restored in front of its own promoter resulting from the complementation allelic exchange mutation experiment and its gene structure is, therefore, similar to the wild type *E. chaffeensis*, except that it also expresses mCherry and gentamicin resistance proteins. This modified *E. chaffeensis*, that is similar to wild type in having the complete genome, will be useful for novel studies in monitoring the pathogen in real time by fluorescence imaging in vitro and in vivo, similar to prior studies described for *Borrelia burgdorferi*.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

EXAMPLES

Example 1

Materials and Methods
In Vitro Cultivation of *E. chaffeensis*.
*E. chaffeensis* Arkansas isolate was continuously cultivated in ISE6 tick cell line, an *I. scapularis* embryonic cell line, as described earlier (Elwell, C., Mirrashidi, K., and Engel, J., *Nat. Rev. Microbial.;* 14, 385-400 (2016). The canine macrophage cell line (DH82) was also used to cultivate *E. chaffeensis* by following the protocols reported earlier (Walker, D. H., Paddocl, C. D. and Dumler, J. S., Med Clin North Am; 92, 1345-1361 (2008)).

Construction for Homologous Recombination Plasmids and Segments.

All the primers used for the preparation of recombinant plasmid constructs developed for the targeted mutagenesis experiments are described in Table 1. Plasmids used and prepared in this study were listed in Table 2.

TABLE 1

List of oligonucleotides used in this study. Uppercase sequences are gene specific; lowercase sequences are Gibson Assembly overlaps.

| Primer* | Sequence | Orientation | Size (bp) |
|---|---|---|---|
| HOMOLOGOUS RECOMBINATION CONSTRUCTS: | | | |
| For Ech_0230 gene disruption | | | |
| Ech_0230 gene segment cloning | | | |
| RRG1591 | TATGGGCCTAAGATAGTATTACC (SEQ ID No. 1) | forward | 2074 |
| RRG1602 | AAGACACACAAGAACATGACACTGCC (SEQ ID No. 2) | reverse | |
| Insertion specific primers to split the plasmid construct of pHR-Ech_0230 | | | |
| RRG1599 | gatcaccaaggtagtcggcaaataactcgagTATATA TAATCATGTATCGATTATATATAACTGTG TGC(SEQ ID No. 3; PRIMER) | forward | 6081 |
| RRG1592 | cctaattaaaaaaagtcaaaattaatagtcacatttttctcga gCTGTAGTACCATGTGTTACTTACCCTCT TTC(SEQ ID No. 4, PRIMER) | reverse | |
| For Ech_0230 gene disruption | | | |
| Ech_0379 gene segment cloning | | | |
| RRG1603 | ACCTGCTGTACTGAGTATGTTCTTG (SEQ ID No. 5) | forward | 2546 |
| RRG1608 | AGACAAGAACATGCTTCAGGTGCTAC (SEQ Id No. 6) | reverse | |
| Insertion specific primers to split the plasmid construct of pHR-Ech_0379 | | | |
| RRG1604 | cctaattaaaaaaagtcaaaattaatagtcacatttttctcga gTGCTGCATTAATTCTATGTAATTATCTTT AG(SEQ ID No. 7-PRIMER) | forward | 6552 |
| RRG1605 | gatcaccaaggtagtcggcaaataactcgagTATTAT GCTTTATAAATGTTCTCAGTCTATTGGC (SEQ ID No. 8-PRIMER) | reverse | |
| For cloning Tuf-2(Ech_0407)promoter | | | |
| RRG1595 | AAAAATGTGACTATTAATTTTGACTTTTTT TAATTAGG(SEQ ID No. 9; PROMOTER) | forward | 387 |
| RRG1596 | gcgatcaccgcttccctcatAAACAAATACCTTTA ACATCATTAAACCATTTC(SEQ ID No. 10; PROMOTER) | reverse | |
| For cloning aadA gene | | | |
| RRG1597 | gaaatggtttaatgatgttaaaggtatttgtttATGAGGG AAGCGGTGATCGC(SEQ ID No. 11) | forward | 789 |

TABLE 1-continued

List of oligonucleotides used in this study.
Uppercase sequences are gene specific; lowercase sequences are Gibson Assembly overlaps.

| Primer* | Sequence | Orientation | Size(bp) |
|---|---|---|---|
| RRG1598 | TTATTTGCCGACTACCTTGGTGATC ID No. 12) | reverse | |
| For Ech_0379 gene function restoration | | | |
| Ech_0379 3' end segment cloning | | | |
| RG8 | GATAATTACATAGAATTAATGCAGCATAT TATGCTTTATAAATGTTCTCAG(SEQ ID No. 13) | forward | 427 |
| RG9 | GCATGCGGCGATCGTTCTAGGAGCTATA AATCTACACTTTCTTCAAC(SEQ ID No. 14) | reverse | |
| For cloning Amtr promoter with mCherry gene(Amtr-mCh) | | | |
| RG10 | CTCCTAGAACGATCGCCGCATGCTAGC (SEQ ID No. 15; PRIMER) | forward | 950 |
| RG11 | AATTTAATCCCTATTTGTATAATTCG (SEQ ID No. 16; PRIMER) | reverse | |
| For cloning gentamycin gene from plasmid pEch_rps1-GENT | | | |
| RG12 | atacaaatagggattaaattATGTTAAGATCATCA AATGATG(SEQ ID No. 17) | forward | 563 |
| RRG914 | ACTACTAGTTTATGTTGCTGTACTTGGAT CAATATC(SEQ ID No. 18) | reverse | |
| Insertion specific primers to split the plasmid construct of pHR-Ech_0379 for rescue construct | | | |
| RG6 | TGCTGCATTAATTCTATGTAATTATCTTTA G(SEQ ID No. 19; PRIMER) | forward | 6499 |
| RG22 | tacagcaacataaactagtagtTATTATGCTTTATA AATGTTCTCAGTCTATTGGC(SEQ ID No. 20; PRIMER) | reverse | |
| PRIMERS FOR MUTANT SCREENING: | | | |
| Ech_0230 disruption mutant | | | |
| PCR I | | | |
| RRG1944 | ATTAGTGCTATGGCATTTGGTC(SEQ ID No. 21) | forward | 1525 |
| RRG1596 | | reverse | |
| PCR II | | | |
| RRG1597 | CAATTTACATGACATACTAACAAGC(SEQ ID No. 22) | forward | 2057 |
| RRG1945 | | reverse | |
| PCR III | | | |
| RRG1944 | | forward | 3582 |
| RRG1945 | | reverse | |
| Ech_0379 disruption mutant | | | |
| PCR I | | | |
| RRG1946 | TGAGTGCTATGATACTCAAAGC(SEQ ID No. 23) | forward | 1779 |
| RRG1596 | | reverse | |
| PCR II | | | |
| RRG1597 | AGAATCAACAAGGCCTACATACC(SEQ ID No. 24) | forward | 2352 |
| RRG1947 | | reverse | |
| PCR III | | | |
| RRG1946 | | forward | 4131 |
| RRG1947 | | reverse | |

TABLE 1-continued

List of oligonucleotides used in this study.
Uppercase sequences are gene specific; lowercase sequences are
Gibson Assembly overlaps.

| Primer* | Sequence | Orientation | Size(bp) |
|---|---|---|---|
| Ech_0379 rescue mutant | | | |
| PCR I | | | |
| RRG1946 | TCCGCAGGATGTTTCACATA(SEQ ID No. 25) | forward | 2243 |
| RG97 | | reverse | |
| PCR II | | | |
| RRG94 | AAGCAAATGCTTTAGGTGCAT(SEQ ID No. 26) | forward | 1711 |
| RRG1947 | | reverse | |
| PCR III | | | |
| RRG1946 | | forward | 4824 |
| RRG1947 | | reverse | |
| SOUTHERN BLOT PROBE AMPLIFICATION PRIMERS: | | | |
| aadA gene probe | | | |
| RRG1200 | GTTACGGTGACCGTAAGGCTT(SEQ ID No. 27; PRIMER) | forward | 603 |
| RRG1201 | CACGTAGTGAACAAATTCTTCCAACTG (SEQ ID No. 28; PRIMER) | reverse | |
| Ech_0379 gene probe | | | |
| RRG1282 | TGAAAATCTGATCGATAGTGCTGTGG (SEQ ID No. 29; PRIMER) | forward | 384 |
| RRG1283 | GGTTGCATTCCCTACAACCTTAG(SEQ ID No. 30; PRIMER) | reverse | |
| RT-PCR PRIMERS: | | | |
| Ech_0230 | | | |
| RG26 | GCTTTGGATTGTTTGTCTTA(SEQ ID No. 31; PRIMER) | forward | 320 |
| RG27 | TCCATCCCATAACAAATCTA(SEQ ID No. 32; PRIMER) | reverse | |
| Ech_0379 | | | |
| RRG1276 | CTAAGGTTGTAGGGAATGCAACC(SEQ ID No. 33; PRIMER) | forward | 376 |
| RRG1277 | ACAAGGTAAGTACCTTGCTTGCTC(SEQ Id No. 34; PRIMER) | reverse | |

*Sequence for the primers was provided only once if a primer is listed multiple times.

TABLE 2

Plasmids and E. coli strains used in this study

| Name | Description | Reference |
|---|---|---|
| pCis mCherry-SS Himar A7 | Himar transposase, mCherry and aadA gene expression driven by Amtr promoter | |
| pHR-Ech_0230 | Ech_0230 homology arms; pCR™2.1-TOPO vector | This study |
| pHR-Ech_0379 | Ech_0379 homology arms, pCR™2.1-TOPO vector | This study |
| pHR-Ech_0230-tuf-aadA | Ech_0230 homology arms, aadA expression driven by tuf-2 promoter, pCR™2.1-TOPO vector | This study |
| pHR-Ech_0379-tuf-aadA | Ech_0379 homology arms, aadA expression driven by tuf-2 promoter, pCR™2.1-TOPO vector | This study |
| pHR-rescue-Ech_0379- | Ech_0379 homology arms, mCherry and gentamycin expression driven | This study |
| Amtr-mCh-Gent | by Amtr promoter, pCR™2.1-TOPO vector | |
| pEch_rpsl-GENT | Codon optimized gentamycin gene for Echrlichia genome, PUC57 vector | GenScript(will submit seq to NCBI) |

Figure 2A:
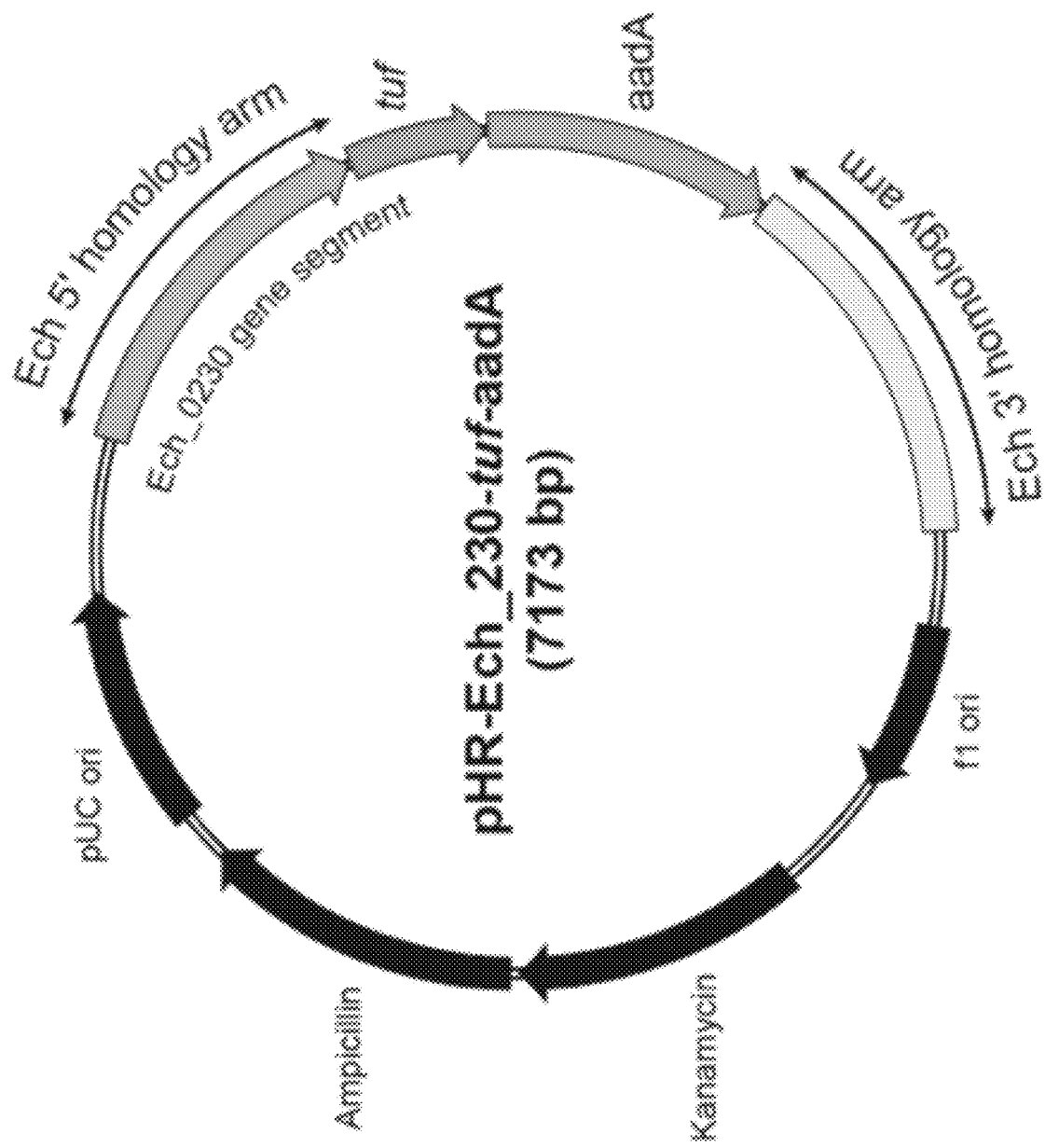
FIG. 2A is a schematic representation of a plasmid map of pHR-Ech_0230-tuf-aadA with an identification of the homology arms. The plasmid sequence data for the construct were deposited in the GenBank (accession #MF068805)
Figure 2B:
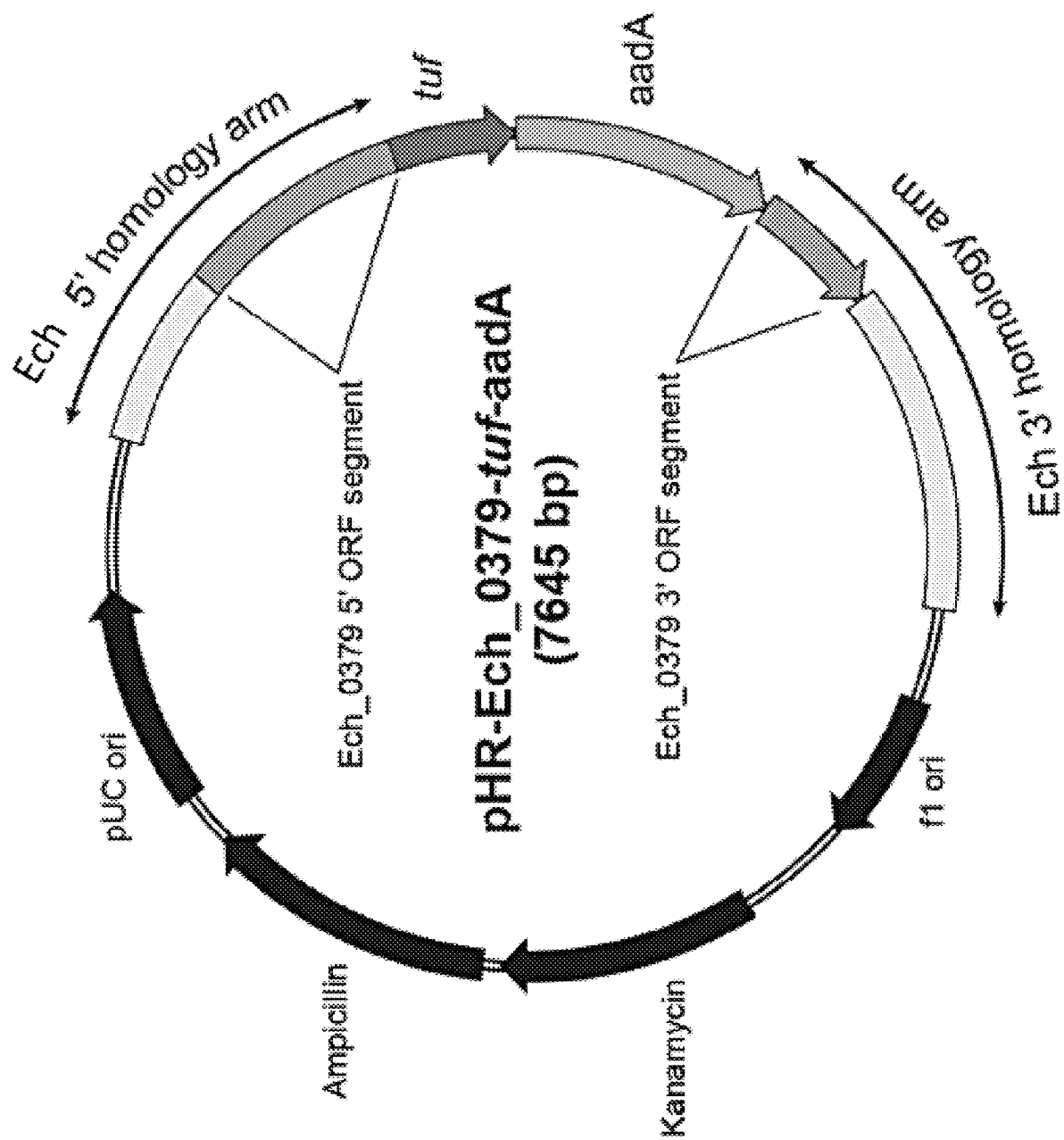
FIG. 2B is a schematic representation of a plasmid map of pHR-Ech_0379-tuf-aadA with an identification of the homology arms. The plasmid sequence data for all the construct were deposited in the GenBank (accession #MF068806).
Figure 3A:
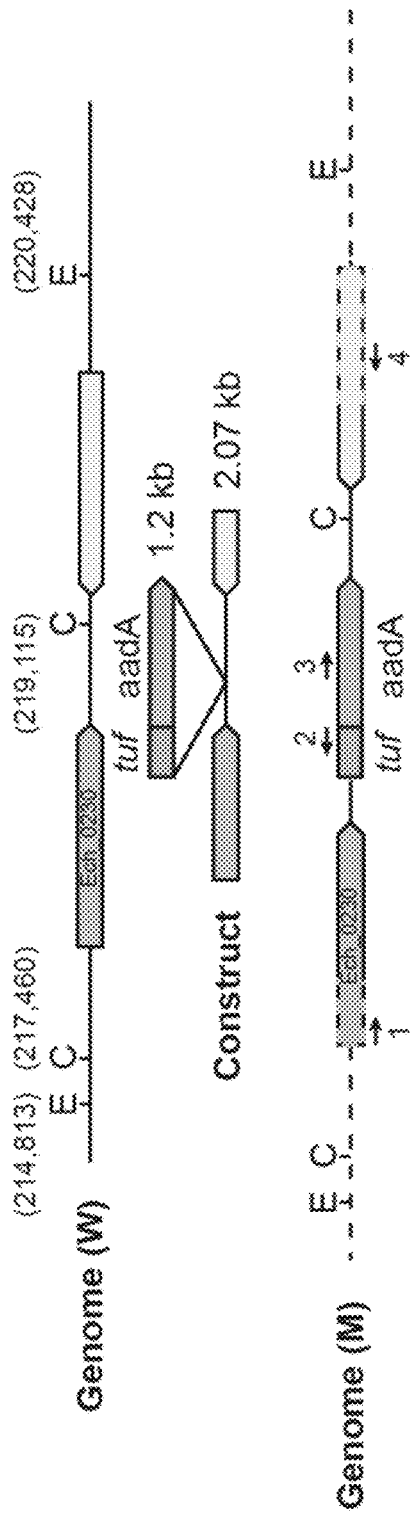
FIG. 3A illustrates targeted allelic exchange mutagenesis to disrupt Ech_0230 gene with FIG. 3A depicting the genomic segment spanning the region selected for preparing an allelic exchange construct, including the restriction enzyme sites (EcoRI (E) and ClaI (C)) used for the mapping the insertion. Genomic coordinates for restriction enzyme sites and the size of inserted fragment (tuf-aadA) were included to allow determination of the expected DNA sizes in PCR and Southern blot analysis.
Figure 3B:
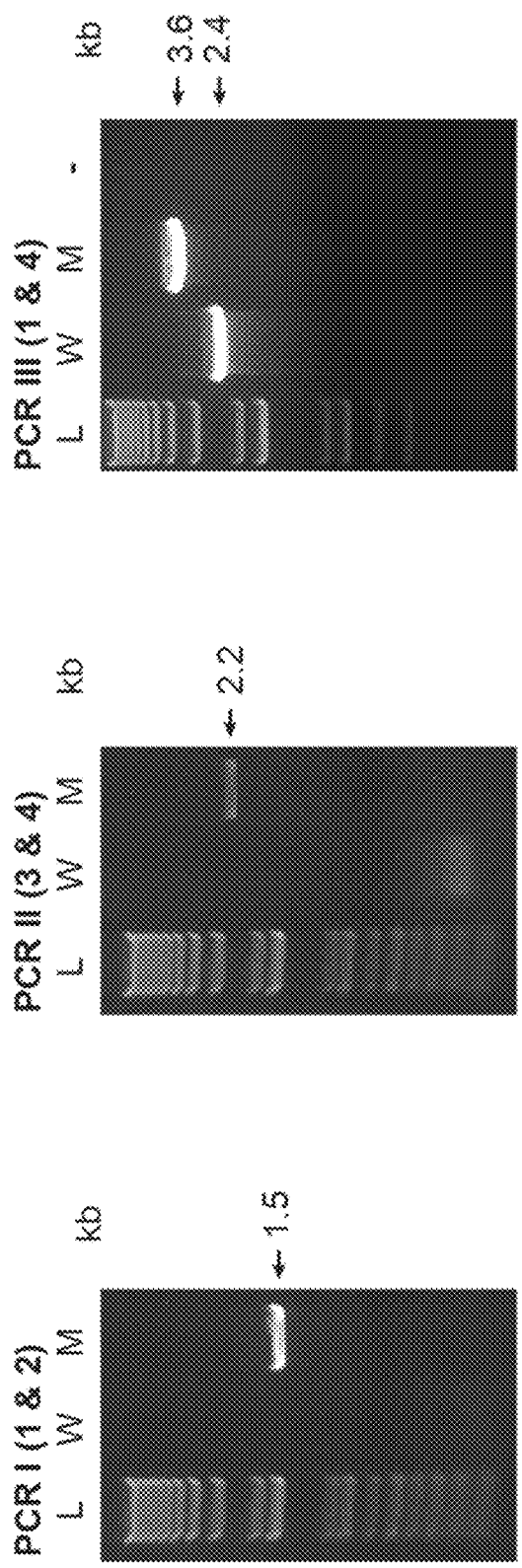
FIG. 3B is a picture showing amplicons resolved following three different PCRs using primers targeting to the genomic regions upstream and downstream to the allelic insertion (primers identified as 1 and 4) and to the inserted DNA (primers; 2 and 3). (L, 1 kb plus molecular weight DNA markers; Wild Type (W), PCR with wild type genomic DNA as the template; Mutant (M), PCR with mutant genomic DNA as the template).
Figure 3C:
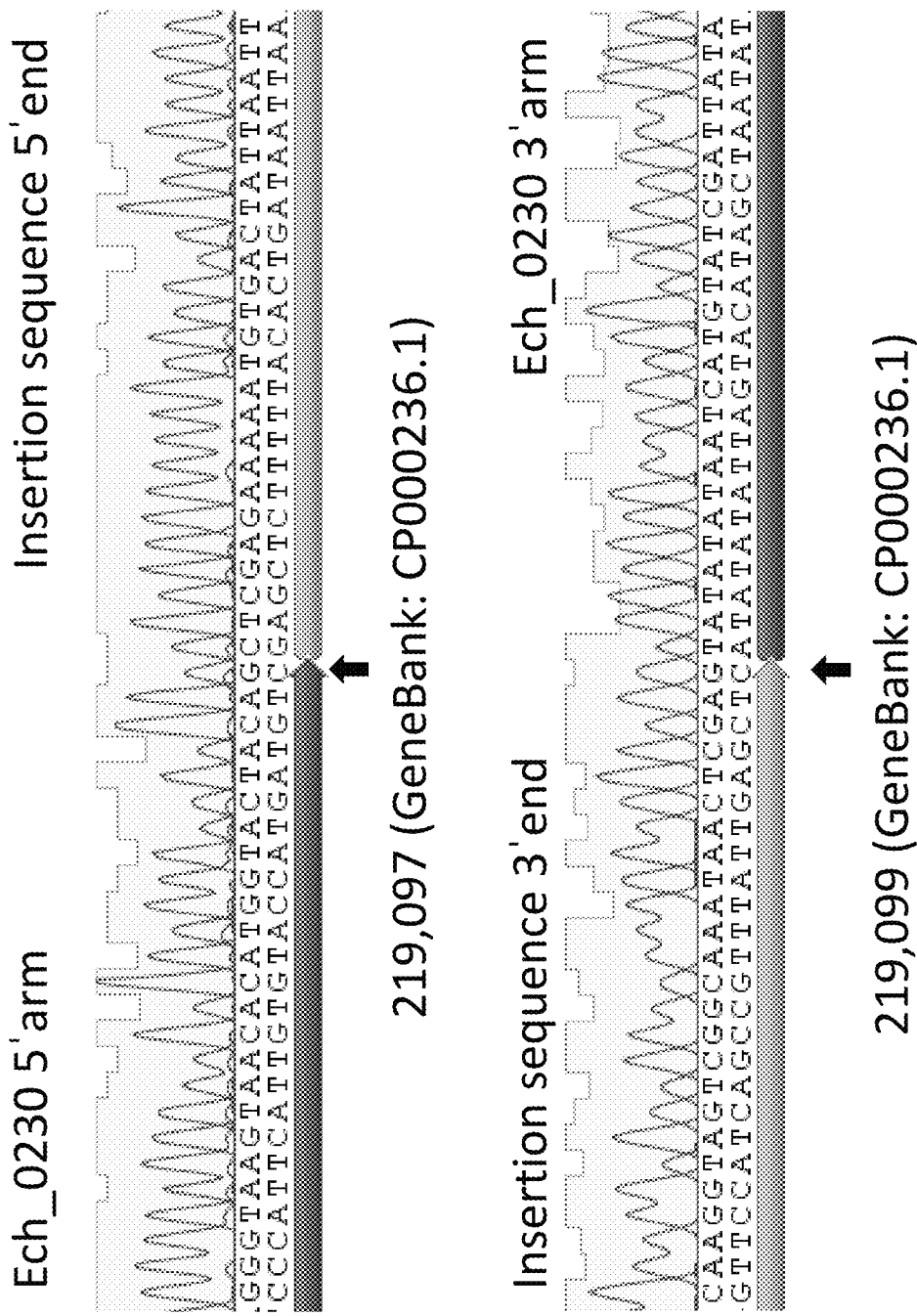
FIG. 3C is an illustration showing PCR DNA Sequence verification of insertion sites in the targeted mutant. In the top panel, the DNA sequence generated from amplicons shown above and to the left of the black arrow represents the sequence from *E. chaffeensis* genome, while the sequence above and to the right of the black arrow represents the inserted sequence in the gene disruption mutant. In the bottom panel, the DNA sequence generated from amplicons shown above and to the right of the black arrow represents the sequence from *E. chaffeensis* genome, while the sequence above and to the left of the black arrow represents the inserted sequence in the gene disruption mutant. Sequences boundaries at the 5' and 3' insertion junctions were identified with a small black arrow lines. Additionally in this top panel, the sequence on top is SEQ ID NO. 42 and the sequence on the bottom is SEQ ID NO. 48. In the bottom panel, the top sequence is SEQ ID NO. 43 and the bottom sequence is SEQ ID NO. 49.
Figure 3D:
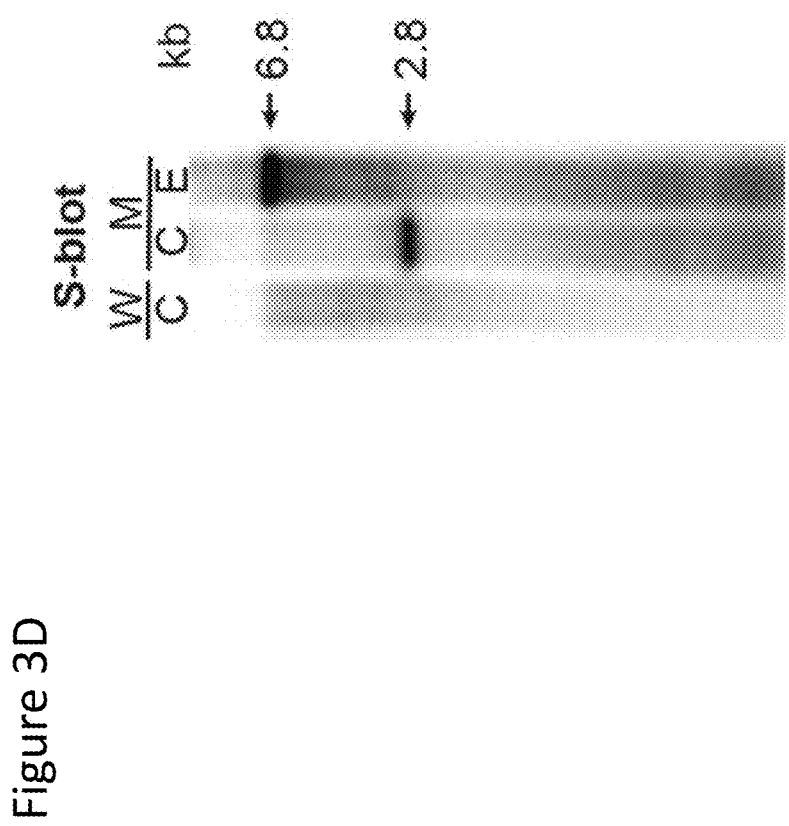
FIG. 3D is a picture of a Southern blot analysis of genomic DNAs (W and M) digested with ClaI (C) or EcoRI (E). The blot analysis was performed with aadA gene segment as the probe.
Figure 4A:
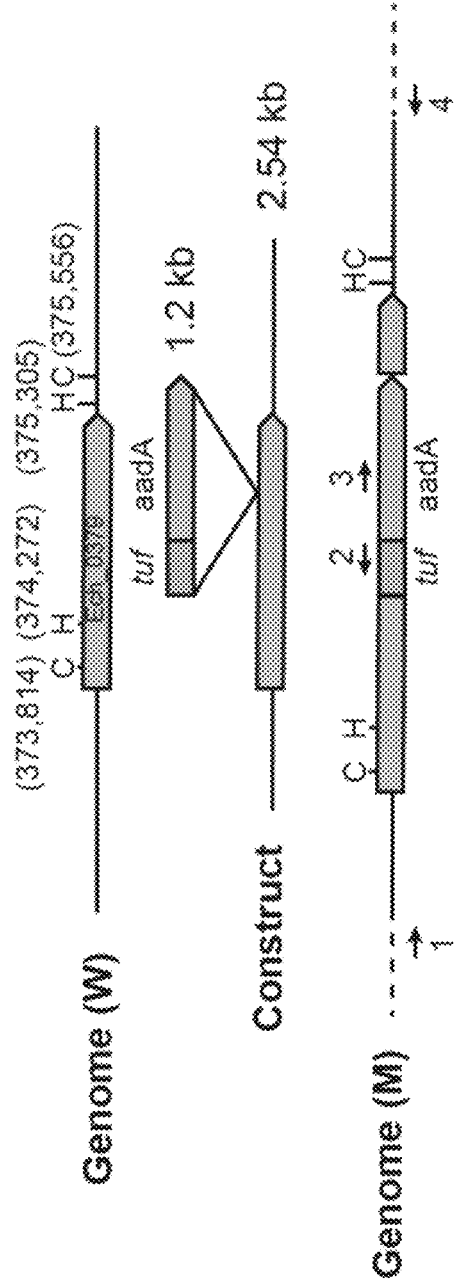
FIG. 4 illustrates targeted allelic exchange mutagenesis to disrupt Ech_0379 gene with FIG. 4A depicting the genomic segment spanning the region selected for preparing an allelic exchange construct, including the restriction enzyme sites (ClaI (C) and HindIII (H)) used for the mapping the insertion. Genomic coordinates for restriction enzyme sites and the size of inserted fragment (tuf-aadA) were included to allow determination of the expected DNA sizes in PCR and Southern blot analysis.
FIG. 4B is a picture showing amplicons resolved following three different PCRs using primers targeting to the genomic regions upstream and downstream to the allelic insertion (primers identified as 1 and 4) and to the inserted DNA (primers; 2 and 3). (L, 1 kb plus molecular weight DNA markers; Wild Type (W), PCR with wild type genomic DNA as the template; Mutant (M), PCR with mutant genomic DNA as the template).
FIG. 4C is an illustration showing PCR DNA Sequence verification of insertion sites in the targeted mutant. In the top panel, the DNA sequence generated from amplicons shown above and to the left of the black arrow represents the sequence from *E. chaffeensis* genome, while the sequence above and to the right of the black arrow represents the inserted sequence in the gene disruption mutant. In the bottom panel, the DNA sequence generated from amplicons shown above and to the right of the black arrow represents the sequence from *E. chaffeensis* genome, while the sequence above and to the left of the black arrow represents the inserted sequence in the gene disruption mutant. Sequences boundaries at the 5' and 3' insertion junctions were identified with a small black arrow lines. Additionally in this top panel, the sequence on top is SEQ ID NO. 44 and the sequence on the bottom is SEQ ID NO. 50. In the bottom panel, the top sequence is SEQ ID NO. 45 and the bottom sequence is SEQ ID NO. 51.
FIG. 4D is a picture of a Southern blot analysis of genomic DNAs (W and M) digested with ClaI (C) and HindIII (H). The blot analysis was performed with aadA gene segment as the probe.
Figure 4B:
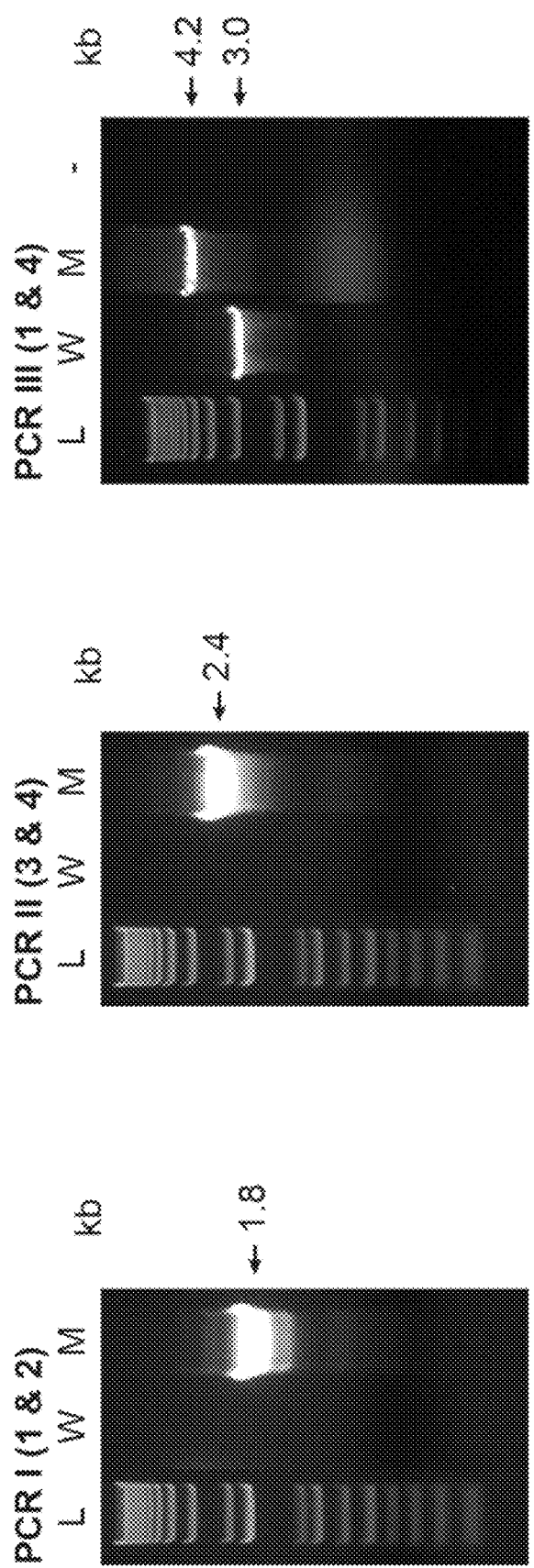
Figure 4C:
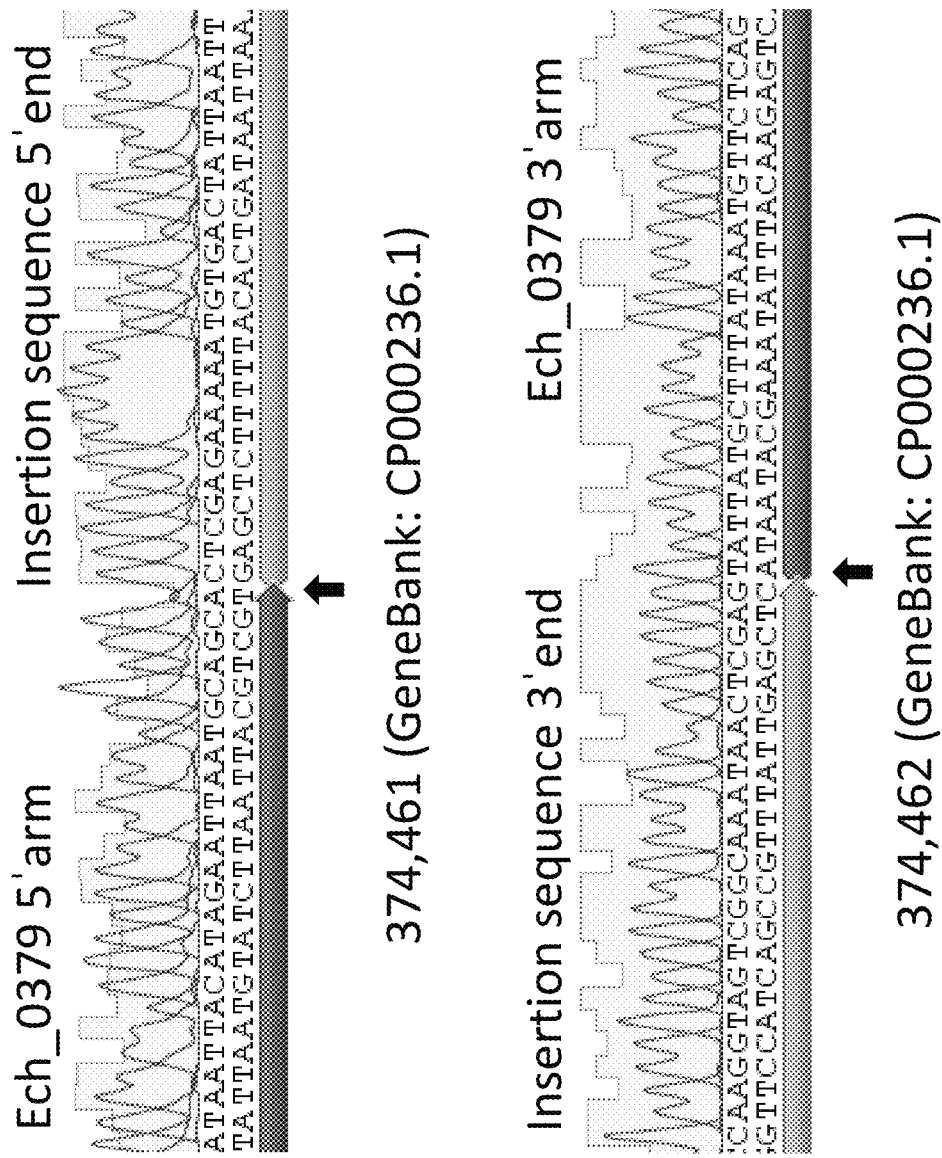
Figure 4D:
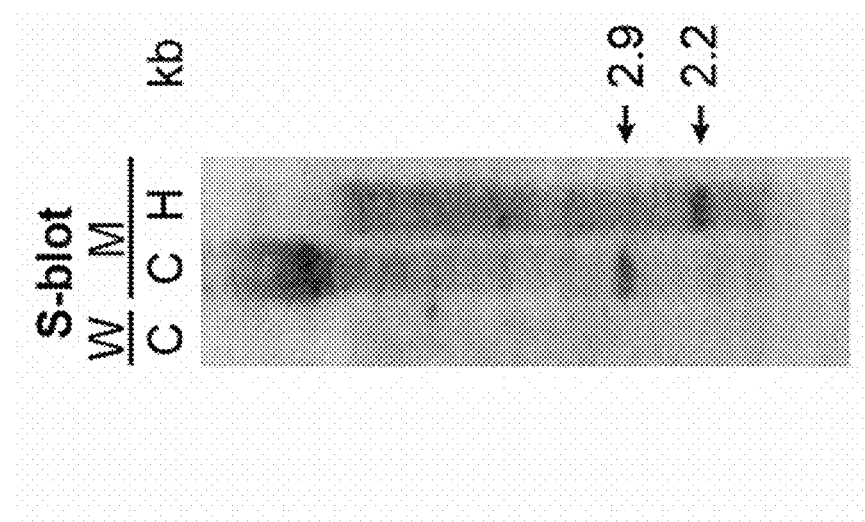

An illustration of the detailed molecular steps followed in preparing the constructs for allelic exchange mutagenesis experiments are depicted in FIG. 1. The Platinum® Taq DNA Polymerase High Fidelity (Invitrogen, Carlsbad, Calif.) was used in all PCR experiments while preparing the constructs. Ech_0230 and Ech_0379 genes of *E. chaffeensis* were used to create allelic exchange mutations as we previously reported random mutations within these genes by Himar1 random mutagenesis method and that the mutant organisms grow normally under in vitro cultures. About 2.0 kb genomic DNA segments spanning about 1 kb each from both sides of the previously identified mutation insertion sites of the genes (referred as A and A' in FIG. 1) were amplified from E. chaffeensis genome (GenBank #CP000236.1; Himar1 mutation insertion sites for Ech_0230 and EcH_0379 are 219,097 and 374,461, respectively). Genome coordinates of the amplified segments of Ech_0230 and Ech_0379 genes are 218,060 to 220,133 and 373,265 to 375,810, respectively. The amplicons were first cloned into the plasmid, pCR™2.1-TOPO TA vector (Life Technologies, Rockville, Md.) by following manufacturer instructions. Tuf-2 gene (Ech_0407) promoter (tuf) spanning 0.37 kb DNA was also amplified from the E. chaffeensis genome (genome coordinates of this segment are 396,385 to 396,751) for use in constitutive expression of the aadA gene product to confer resistance to spectinomycin and streptomycin. The aadA gene open reading frame (ORF) was obtained by PCR from pCis mCherry-SS Himar A7 plasmid (Sahni, S. K., Narra, H. P., Sahni, A., and Walker, D. H.; Future Microbiol; 8, 1265-1288 (2013).) The tuf promoter and aadA ORF were also cloned into a separate pCR™2.1-TOPO TA vector and the plasmid was then used to generate linear fragments of tuf-aadA segment (fragment 1) for incorporation into the final targeted gene disruption mutagenesis constructs. Linear fragments were then generated from the entire plasmids (pHR-Ech_0230 and pHR-Ech_0379 respectively) containing the gene segments using Ech_0230 or Ech_0379 gene specific primers designed to split these gene fragments to two equal halves positioned at each end of the linear fragments and keeping the plasmid backbone in the middle (fragment 2). By following the protocols of Gibson Assembly method (New England Biolabs, Ipswich, Mass.), the linear fragments 1 and 2 were then ligated to create the final homologous recombinant plasmid constructs, where the gene segments were disrupted with the insertion of tuf-aadA segments. The final constructs were named as pHR-Ech_0230-tuf-aadA and pHR-Ech_0379-tuf-aadA, respectively (FIGS. 2A and 2B, respectively). (GenBank submission #s 2012015 and 2012023; accession numbers are yet to be received.) Subsequently, linear fragments from these constructs containing both the 5' and 3' homology arms of each gene disruption segments along with the tuf-aadA cassette were generated by PCR (FIG. 3A). The amplicons were then resolved on a 1% agarose gels (FIG. 3B); DNAs were gel isolated and concentrated to 1 µg/µl in nuclease free water for use in the allelic exchange mutagenesis experiments to create targeted gene disruptions.

Figure 2C:
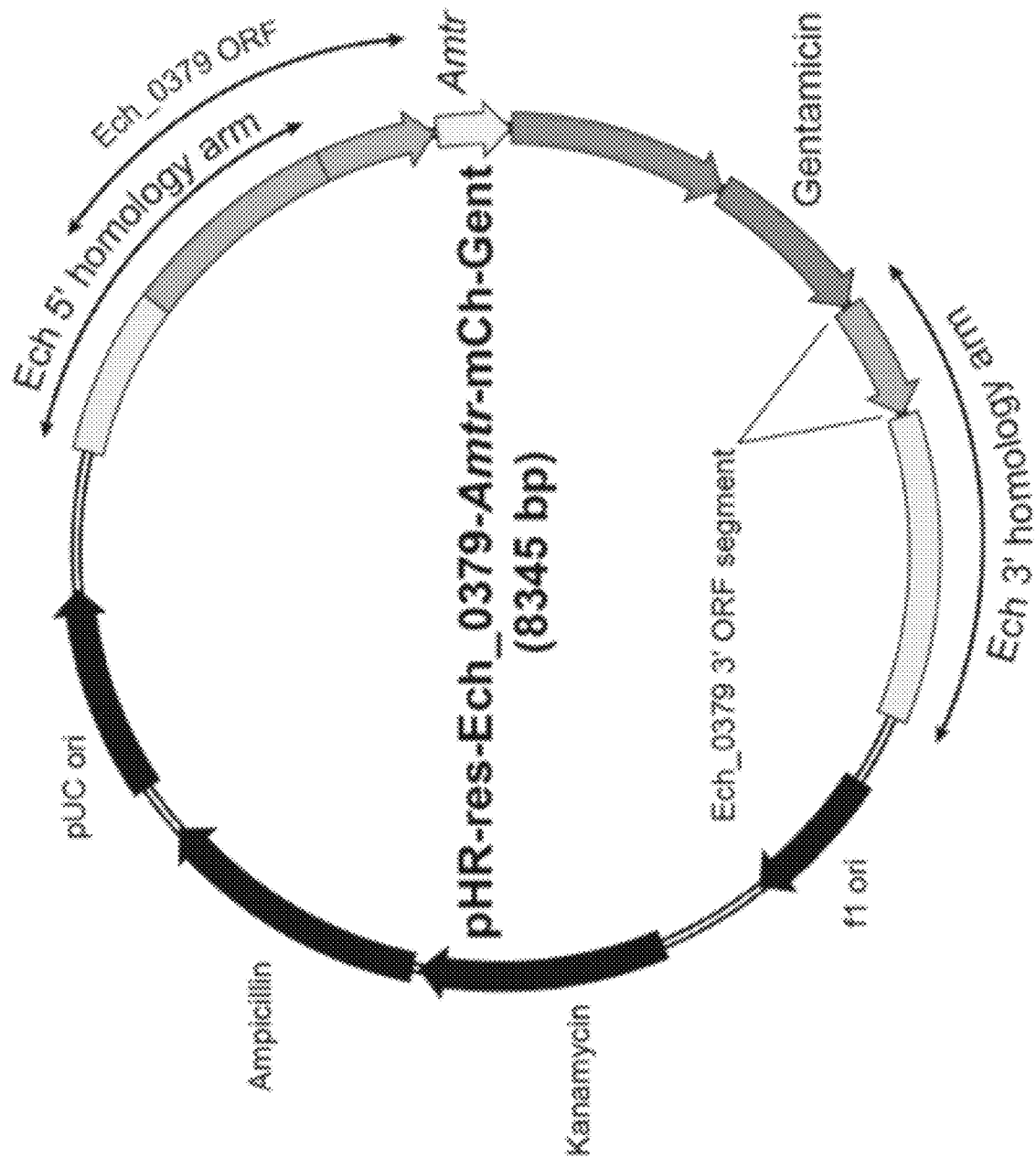
FIG. 2C is a schematic representation of a plasmid map with an identification of the homology arms. The plasmid sequence data for the construct was deposited in the GenBank (accession #MF068807).

For constructing the Ech_0379 gene function rescue template, the 3' end 0.5 kb fragment downstream from the mutation site by PCR using E. chaffeensis genomic DNA was generated as the template (genomic coordinates are 374,462 to 374,837). The Amtr-mCherry (Amtr-mCh) DNA segments constituting the Anapmasma marginale transcription regulator (Tr) gene promoter and mCherry ORF were amplified using pCis mCherry-SS Himar A7 plasmid as the template. The gentamicin resistance gene coding sequence (Gent) was codon optimized commercially (GenScript, Piscataway, N.J.) (GenBank #KY977452) as per the frequently found codons of E. chaffeensis genome. The Gent segment was then used to clone downstream to Amtr-mCh fragment to generate Amtr-mCh-Gent fusion fragment. The 3' end 0.5 kb Ech_0379 segment was then ligated at the 5' end of the Amtr-mCh-Gent fragment by performing overlapping PCR and the final amplicon was subsequently cloned into the Ech_0379-tuf-aadA-HR 1 construct to replace the tuf-aadA segment with Amtr-mCh-Gent segment containing the 3' end 0.5 kb Ech_0379 ORF segment by performing the Gibson Assembly cloning strategy. The final Ech_0379 rescue plasmid construct; pHR-res-Ech_0379-Amtr-mCh-Gent included the full length Ech_0379 ORF restored in front of its own promoter, followed by the Amtr-mCh-Gent and the 3' end 1 kb genomic segment of Ech_0379 gene (FIG. 2C) (GenBank submission #2012033; accession number is yet to be received). This construct was then used as the template to generate linear fragments by PCR which contained the entire Ech_0379 gene at the 5' end, including its own promoter and the complete ORF, followed by Amtr-mCh-Gent segment and the additional 3' end 1 kb segment downstream from Ech_0379 gene mutation site (FIG. 5A). The PCR product was purified by QIAquick PCR Pruification Kit (Qiagen, Hilden, Germany) and concentrated to 1 µg/µl in nuclease-free water as outlined above for use in the allelic exchange mutagenesis experiment to restore the integrity of the gene in E. chaffeensis organisms having Ech_0379 gene disruption.

Purification of Cell-Free E. chaffeensis Organisms.

Five ml of E. chaffeensis cell culture from about 80-90% infected confluent ISE6 cell culture flask was used to generate host cell-free E. chaffeensis organisms. Briefly, the infected cell suspension was recovered by centrifugation at 15,000 g for 10 min at 4° C. and after discarding the supernatant, 1.5 ml of ice-cold 0.3 M sucrose solution and 100 µl volume of autoclaved rock tumbler grit #1 (60/90 grit silicon carbide, Lortone, Wash.) were added to the cell pellet and votexed using a table top vortexer at maximum speed for 30 sec to release bacteria from the infected host cells. The cell suspension was then centrifuged at 200 g for 10 min at 4° C. to pellet the host cell debris. The supernatant was carefully recovered into a 3 ml syringe and passed through a 1.6 µm filter (Whatman Ltd., Piscataway, N.J.); the filtrate containing E. chaffeensis organisms were pelleted by centrifuging at 15,000 g for 10 min at 4° C. The cell pellet was washed twice with 0.3 M ice-cold sucrose solution resuspended in 45 µl of 0.3 M ice-cold sucrose solution and used immediately for electroporation experiments.

Transformation of E. chaffeensis and Clonal Isolation of Mutants.

Between 3-10 µg of purified linear DNA fragments from the allelic exchange mutagenesis plasmid constructs (outlined above) were added to the host cell-free E. chaffeensis organisms in 45 µl volume, mixed gently and transferred the contents into a 1 mm gap electroporation cuvette (Bio-Rad Laboratories, Hercules, Calif.). The cuvette was incubated on ice for 15 min and then subjected to electroporation at 2,000 volts, 25 µF and 400 S2 setting (Gene Pulser Xcell™, Bio-Rad Laboratories, Hercules, Calif.). The electroporated cells were transferred to a micro centrifuge tube containing 0.5 ml of FBS and 1 ml of uninfected ISE6 cell suspension containing about $1 \times 10^6$ ISE6 cells in tick cell culture infection media. The mixed sample was centrifuged at 5,000 g for 5 min, incubated at room temperature for 15 min, cells were then resuspended in 5 ml culture media and the entire contents were transferred to a T25 flask containing confluent ISE6 cells and incubated for 24 h in a humidified 34° C. incubator and then 100 µg/ml each of spectinomycin and streptomycin were added to the culture medium; incubations were continued at 34° C. for several weeks to select mutants. Typically, mutants were detected by PCR analysis after two to three weeks, although the assessment continued for several weeks beyond this time point. Similar experiment was carried out to obtain Ech_0379 gene restoration mutant, except that the media containing 80 µg/ml of gentamicin were used after 24 h of electroporation. Ech_0379 gene restoration mutant cultures were also assessed by detecting the expression of mCherry by examining the cultures using a Nikon Diaphot inverted microscope (Nikon, Melville, N.Y.). Once identified, the antibiotic resistant cultures were transferred to DH82 cell cultures for further growth and maintenance. Liquid nitrogen stocks were also prepared and stored within the first two weeks after the establishment of mutant strains.

Confirming the Presence of *E. chaffeensis* Mutants.

The cultures of *E. chaffeensis* which grew well in the presence of antibiotics were subsequently screened for allelic exchange mutation positives by genomic DNA analysis by insertion specific PCRs. Total genomic DNAs were recovered from the cultures using a Wizard Genomic DNA Purification Kit as per the manufacturer's instructions (Promega, Madison, Wis.). Three different PCR assays were performed using the purified genomic DNAs (FIG. 4B). The first and second PCR assays (FIG. 4B first panel) targeted to 1) the genomic region 5' to the allelic exchange sites and to the insertion specific DNA (FIG. 4B second panel) the insertion DNA and to the 3' of the allelic exchange sites on the genome. The $3^{rd}$ PCR assay (FIG. 4B third panel) was designed to also test the clonal purity of mutants; primers used in this assay were targeted to the genomic regions upstream and downstream of the allelic exchange insertion sites (FIG. 4C). The PCR products were resolved on a 0.9% agarose gel to identify specific predicted length amplicons and then subjected to sequencing analysis to further confirm the integrity by mapping the genomic junctions of the insertions from both ends of the amplicons. Mutations and clonal purity was subsequently confirmed by Southern blot analysis (FIG. 4D). Genomic DNAs from the mutant organisms and from wild-type organisms were subjected to restriction enzyme digestions using ClaI, EcoRI or HindIII restriction enzymes; the digested DNAs were resolved on a 1% agarose gel and transferred to a nylon membrane (Roche Diagnostics, Indianapolis, Ind.). The insertion specific aadA gene segment probe was used in the Southern blot hybridization experiment to locate inserted DNA in targeted disrupted mutants of Ech_0230 and Ech_0379, while Ech_0379 gene segment probe was used for locating the genomic insertions in targeted gene insertion and restoration mutant clones of Ech_0379 as per standard procedures of DNA blot analysis.

RNA Analysis by RT-PCR to Verify the Loss and Restoration of Transcription.

Total RNAs from wild type and mutant *E. chaffeensis* organisms grown in ISE6 or DH82 cell cultures were isolated by following the Tri-reagent total RNA isolation method as per the manufacturer's instructions (Sigma-Aldrich, St. Louis, Mo.). The RNA samples were then treated with RQ1 DNase (Promega, Madison, Wis.) at 37° C. for 60 min to remove any residual genomic DNAs. Primers targeting to Ech_0230 or Ech_0379 ORF were used in RT-PCR analysis and the presence of specific amplicons was assessed by 0.9% agarose gel analysis and by subjecting the products to DNA sequence analysis. Semi quantitative RT-PCR assays were performed as we previously described for assessing the mRNA expression from the genes Ech_0378, Ech_0379 and Ech_0380 using equal quantities of *E. chaffeensis* RNAs recovered from wild type, Ech_0379 gene disruption, and Ech_0379 gene restoration mutants (FIGS. 5B, 5C, 6A, and 6B). The assays were performed at 30, 35 and 40 cycles (FIG. 6C). Southern blot was used to confirm (FIG. 5E).

Example 2

Materials and Methods In vitro cultivation of *E. canis* and *Anaplasma phagocytophilum*. *E. canis* and *A. phagocytophilum* are continuously cultivated in ISE6 tick cell line, an *I. scapularis* embryonic cell line, as described earlier (Munderloh, U. G. et al. J. Clin. Microbiol. 37, 2518-2524 (1999) and Cheng, C. & Ganta, R. R. *Curr. Protoc. Microbiol.* Chapter 3, Unit 3A 1 (2008)).

Construction for Homologous Recombination Plasmids and Segments.

All the primers used for the preparation of recombinant plasmid constructs are developed for the targeted mutagenesis experiments by following similar protocols as we described for *E. chaffeensis*, except that the pathogens' gene target specific primers are used. Similarly, the detailed molecular steps followed in preparing the constructs for allelic exchange mutagenesis experiments are similar to those depicted for *E. chaffeensis* by following standard molecular methods (Sambrook, J. & Russell, D. W. Molecular cloning: a laboratory manual. Cold Spring Harbor Laboratory, Cold Spring Harbor, N.Y. (2001)). Briefly, about 2.0 kb genomic DNA segments spanning about 1 kb each from both sides of the previously identified mutation insertion sites of the genes are amplified from *E. canis* or *A. phagocytophilum* gene homologs that are similar to *E. chaffeensis* gene Ech_0660. The Ech_0660 homolog sequences of *E. canis* and *A. phagocytophilum* are provided herein as SEQ ID NO. 54 and SEQ ID NO. 55, respectively. The amplicons are first cloned into a plasmid vector and the *Ehrlichia* or *Anaplasma* gene promoter driving antibiotic selection marker gene, along with a fluorescent reporter gene are inserted into the final targeted gene disruption mutagenesis constructs to split the sequence of the bacteria to about equal halves. Linear fragments are then generated by PCR from the entire recombinant plasmids containing *E. canis*- or *A. phagocytophilum*-specific disruption gene segments. The amplicons are then purified and concentrated to 1 μg/μl in nuclease free water for use in the allelic exchange mutagenesis experiments to create targeted gene disruptions.

Purification of Cell-Free *E. canis* and *A. phagocytophilum* Organisms.

Purification method to recover host cell-free organisms of *E. canis* or *A. phagocytophilum* is essentially the same as *E. chaffeensis* described above in Example 1 except that the infected 80-90% infected confluent ISE6 cell culture flasks containing *E. canis* or *A. phagocytophilum* are used, respectively, to generate the specific host cell-free organisms by following the protocol as in Felsheim, R. F. et al. *BMC Biotechnol.* 6, 42 (2006).

Transformation of *E. chaffeensis* and Clonal Isolation of Mutants.

Three μg of purified linear DNA fragments from the allelic exchange mutagenesis plasmid constructs (outlined above) were added to the host cell-free *E. chaffeensis* organisms in 45 μl volume, mixed gently and transferred the contents into a 1 mm gap electroporation cuvette (Bio-Rad Laboratories, Hercules, Calif.). The cuvette was incubated on ice for 15 min and then subjected to electroporation at 2,000 volts, 25 μF and 400 S2 setting (Gene Pulser Xcell™, Bio-Rad Laboratories, Hercules, Calif.). The electroporated cells were transferred to a micro centrifuge tube containing 0.5 ml of FBS and 1 ml of uninfected ISE6 cell suspension containing about $1\times10^6$ ISE6 cells in tick cell culture infection media. The mixed sample was centrifuged at 5,000 g for 5 min, incubated at room temperature for 15 min, cells were then resuspended in 5 ml culture media and the entire contents were transferred to a T25 flask containing confluent ISE6 cells and incubated for 24 h in a humidified 34° C. incubator and then 100 µg/ml each of spectinomycin and streptomycin were added to the culture medium; incubations were continued at 34° C. for several weeks to select mutants. Typically, mutants were detected by PCR analysis after two to three weeks, although the assessment continued for several weeks beyond this time point. Similar experiment was carried out to obtain Ech_0379 gene restoration mutant, except that the media containing 80 µg/ml of gentamicin were used after 24 h of electroporation. Ech_0379 gene restoration mutant cultures were also assessed by detecting the expression of mCherry by examining the cultures using a Nikon Diaphot inverted microscope (Nikon, Melville, N.Y.). Once identified, the antibiotic resistant cultures were transferred to DH82 cell cultures for further growth and maintenance. Liquid nitrogen stocks were also prepared and stored within the first two weeks after the establishment of mutant strains.

Confirming the Presence of *E. canis* or *A. phagocytophilum* Mutants.

The cultures of *E. canis* or *A. phagocytophilum* which grow well in the presence of antibiotics are screened for allelic exchange mutation positives by genomic DNA analysis by insertion specific PCRs. The protocols are the same as we described for *E. chaffeensis*.

RNA Analysis by RT-PCR to Verify the Loss and Restoration of Transcription.

Total RNAs from wild type and mutant *E. canis* or *A. phagocytophilum* organisms grown in ISE6 cell cultures are isolated by following the TRI-reagent total RNA isolation method and treated with RQ1 DNase. Pathogen gene specific primers are used in RT-PCR analysis and the presence of specific amplicons is assessed by agarose gel analysis and by subjecting the products to DNA sequence analysis (Sambrook, J. & Russell, D. W. Molecular cloning: a laboratory manual. Cold Spring Harbor Laboratory, Cold Spring Harbor, N.Y. (2001)).

Example 3

Materials and Methods

In Vitro Cultivation and Cell-Free *E. chaffeensis* Recovery

*E. chaffeensis* Arkansas isolate wildtype and the mutants were grown in the canine macrophage cell line, DH82. Isolation and purification of cell-free *E. chaffeensis* wildtype and its mutants were carried out as follows. Briefly, the bacterial infection rate in DH82 cells was assessed with Diff-Quik staining. After 72 h of infection when the infection reached to about 80-90%, the culture from four T-150 confluent flasks was harvested and centrifuged at 500×g for 5 min. Cellular pellets were resuspended in 1×phosphate buffered saline (PBS) containing protease inhibitors (Roche, Indianapolis, Ind.) and cells were homogenized on ice by passing through, 15-20 strokes with a 23 g needle in a 10 mL syringe. Efficiency of homogenization, 80-90% lysis, was checked under light microscope. Whole cell lysate was centrifuged at 500×g for 5 min at 4° C. The resulting supernatant containing cell-free *Ehrlichia* organisms was filtered through a 2 μm sterile membrane filter (Millipore, Billerica, Mass.). Cell-free *Ehrlichia* from filtrates were pelleted by centrifuging at 15,000×g for 15 min and the pellet was suspended in PBS and then layered onto 30% diatrizoate meglumine and sodium solution (Renografin) MD-76R (Mallinckrodt Inc, St. Louis, Mo.). The suspension was centrifuged for 1 h at 100,000×g at 4° C. in a S50-ST swinging bucket rotor (Beckman, Indianapolis, Ind.). The pellet of cell-free *Ehrlichia* were washed at 15,000×g for 15 min and used for experiments.

Bacterial mRNA Enrichment and Sequencing

Bacteria mRNA enrichment and cDNA library preparation and RNA sequencing were performed as follows: Briefly, RNA from wildtype and mutants were isolated from purified cell-free *Ehrlichia* using TRIzol Reagent (Sigma-Aldrich, St. Louis, Mo.). RNA samples were then treated with DNase I (Invitrogen, Carlsbad, Calif.) and bacterial RNA was enriched by removing host 18 S rRNA, 28 S rRNA, and polyadenylated mRNA using MICROBEnrich Kit (Ambion, Foster City, Calif.). The quantity and integrity of bacterial RNA before and after enrichment was assessed using a NanoDrop 2000 spectrophotometer (Thermo Scientific, Waltham, Mass.) and Agilent 2100 Bioanalyzer (Agilent Technologies, Santa Clara, Calif.). The Ribo-Zero Magnetic Kit was used to isolate mRNA from total RNA samples and then fragmented into short fragments as per the manufacturer's protocols (Epicentre, Madison, Wis.). Subsequently, cDNA was synthesized using the mRNA fragments as templates. Libraries of cDNAs for wildtype and mutants were prepared using the TruSeq RNA Sample Prep Kit (Illumina, Ingolstadt, Germany). Sample libraries were quantified using Agilent 2100 Bioanaylzer and library quality was assessed by Real-Time PCR (ABI StepOnePlus) prior to subjecting the samples to sequencing on Illumina HiSeq™ 4000 (Beijing Genomics Institute (BGI), Philadelphia, Pa.).

Bioinformatics Analysis

The original image data were transferred into raw sequence data via base calling. Raw reads were subjected to quality assessment to determine whether the raw reads were qualified for mapping. The bases with low quality (<20) were excluded from the analysis. Raw reads were then filtered to remove adapter sequences and low quality reads, then clean reads were aligned to the *E. chaffeensis* Arkansas strain complete genome as per the first annotated GenBank #CP000236.1 using SOAPaligner/SOAP2. This accession number was selected and used because our prior publications, and similarly other investigators, widely used it for referring to gene names and numbers listed in it. Not more than five mismatches were allowed in the alignment, which is a standard cut off used for the alignment analysis. The alignment data were used to calculate distribution of reads on reference genes and determine the gene coverage. Alignment results were assessed for quality check and then proceed with analysis of DGE. The gene expression level was calculated using RPKM method of normalizing for total read length and the number of sequencing reads. We used p-value<0.05, False Discovery Rate (FDR)≤0.001, and the absolute value of Log 2 Ratio≥1 as the threshold to judge the significance difference in gene expression. The FDR uses accurate p-values as a measure of control in multiple sample comparison of RNA seq data. Corrections for false positive and false negative errors were performed using the method described by Benjamini and Yekutieli.

Quantitative Real-Time Reverse Transcription PCR

SYBR green detection-based quantitative real-time reverse transcription PCR (qRT-PCR assays were performed to validate the gene expression changes observed in the RNA seq data analysis). Wildtype, ECH_0379, ECH_0490, and ECH_0660 mutants' RNAs used in generating the RNA seq data were also used to determine transcript levels by performing quantitative RT-PCR by SYBR Green assays using a SUPERSCRIPT® III Platinum SYBR Green One-Step qRT-PCR Kit (Invitrogen, Carlsbad, Calif.). RNA was reverse transcribed from all the replicates using SuperScript III and then quantitative-PCRs were performed in a 25 µL reaction containing 0.5 µM each of forward and reverse primers. Thermal cycler conditions were; 94° C. for 15 sec, 60° C. for 30 sec, and 74° C. for 15 sec for 40 cycles. Thirteen randomly selected differentially transcribed genes were used in validation experiments using StepOnePlus™ Real-Time PCR instrument (Applied Biosystems, Foster City, Calif.) and the data were analyzed by StepOne Software v2.3. *E. chaffeensis* 16 S rRNA was quantitated by real-time RT-PCR and used for normalization of RNA concentrations among different RNA batches, prior to performing the validation experiments. For qRT-PCR data, the delta-delta Ct (ΔΔCt) calculation was employed to calculate relative change in the expression and fold change was obtained by averaging the replicate values of gene expression and the standard error. Semi-quantitative one-step RT-PCR (Life Technologies, Carlsbad, Calif.) targeting to *E. chaffeensis* genes ECH_0490 and ECH_0492 near the transposon mutation downstream to ECH_0490 gene was performed with 30 cycles of amplification using the gene specific primers as described in a previous study (*PLoS One;* 10, e0132657 (2015)). Briefly, RNA from wildtype and ECH_0490 mutant were used as the templates for RT-PCR. One tube without reverse transcriptase or template RNA was used as negative control. One tube with DNA as the template was used as positive control. Thermal cycler conditions were as follows: 50° C. for 1 h for reverse transcription step then followed by 35 cycles of 94° C. for 30 sec, 55° C. for 30 sec, and 72° C. for 30 sec; finally a 2-min 72° C. extension step was part of the reaction.

The rickettsial pathogen *Ehrlichia chaffeensis* causes a tick-borne disease, human monocytic ehrlichiosis. Mutations within certain genomic locations of the pathogen aid in understanding the pathogenesis and in developing attenuated vaccines. Our previ Results Isolation and Purification of Cell-Free *E. chaffeensis* from Host Cells The major challenge of undertaking transcriptome studies of intracellular pathogens is the difficulty in isolating host-cell free bacteria and subsequently recovering high-quality bacterial RNA. Rickettsial organisms, including *E. chaffeensis*, constitute only a very small fraction of isolated total RNA. Because of the presence of highly abundant host cell RNA, recovery of bacterial RNA is a challenge for executing RNA seq analysis experiments. In this study, we first purified the host cell-free bacteria from infected host cells (canine macrophage cell line, DH82) by employing an efficient cell lysis method, coupled with density gradient centrifugation protocols. Host cell lysis was performed to efficiently rupture the host cells without causing a major damage to the bacteria. *E. chaffeensis* organisms are about 0.5 to 1 μm in diameter. Therefore, infected host cell lysate was filtered through 2 μm membrane to remove most of the host cell debris. A high-speed Renografin density gradient centrifugation of the resulting *E. chaffeensis* cell suspension aided in pelleting bacteria while host cell debris remained at the top layer of the solution. After total RNA isolation and DNase treatment, Bioanalyzer analysis revealed that despite the prior fractionation of host cell-free bacteria, the host 28 S and 18 S RNA remained at high concentrations in the recovered RNA. Bacterial mRNA enrichment was carried out by depleting the host poly(A) RNA and eukaryotic ribosomal RNA using a bacterial RNA enrichment protocol, resulting in nearly undetectable levels of host 28 S and 18 S RNA. The absence of contaminating *E. chaffeensis* genomic DNA in the purified RNA samples was confirmed by real-time quantitative PCR using *E. chaffeensis* 16 S rRNA gene primers. We also confirmed the absence of DNA sequences in the RNA seq raw data by aligning 20 randomly selected *E. chaffeensis* intergenic non-coding DNA sequences (data not shown).

Ubiquitous Transcription of Genes in *E. chaffeensis* Mutants

Illumina HiSeq. 4000 RNA seq of *E. chaffeensis* wildtype and mutants generated between 75-130 million reads. The transcriptome data were deposited in the NCBI Bio-Project ID:PRJNA428837 and SRA accession:SRP128532 (found on the web at the ncbi.nlm.nih.gov/sra/SRP128532 site). Despite efficient depletion of host ribosomal RNA, only a fraction (less than 19%) of reads were mapped to *E. chaffeensis* genomes. Mapping of reads (10 reads minimum/gene) identified about 66-80% of the genes being expressed from the *Ehrlichia* genome as per the annotated genome (GenBank #CP000236.1); the transcriptome of wildtype organisms (n=3) contained transcripts for about 920 genes of the total of 1158 genes, and similarly 888, 895, and 768 gene transcripts (n=3) were identified in mutant organisms ECH_0660, ECH_0379, and ECH_0490, respectively (Table 3). The replicate RNA seq data of wildtype ($R^2$=0.9) and mutants ECH_0379 ($R^2$=0.93), ECH_0490 ($R^2$=0.68) and ECH_0660 ($R^2$=0.89) showed a high degree of expression correlation. The scatter plot expression data of wildtype vs. ECH_0379 ($R^2$=0.18) and wildtype vs. ECH_0490 ($R^2$=0.38) showed a negative correlation. Notably, the expression plot of wildtype vs. ECH_0660 showed a positive correlation ($R^2$=0.96). Only transcripts with reads per kilobase transcriptome per million mapped reads (RPKM) ≥1 were considered for differential expression analysis.

TABLE 3

| | No. of genes identified (>3 RPKM, 10 reads minimum) | | | |
|---|---|---|---|---|
| | Replicate 1 | Replicate 2 | Replicate 3 | Avg (std dev) |
| Wildtype | 888 | 900 | 973 | 920 (46) |
| ECH_0379 | 920 | 882 | 883 | 895 (21) |
| ECH_0490 | 841 | 670 | 793 | 768 (88) |
| ECH_0660 | 780 | 917 | 969 | 888 (97) |

Global Transcriptome of *E. chaffeensis*

Distribution of the transcripts in wildtype *E. chaffeensis* included 481 transcripts represented by less than five transcripts, followed by hypothetical protein transcripts (178) representing 19% of transcriptome, and 127 ribosomal protein gene transcripts (14%). Transcripts of major outer membrane proteins (22 transcripts) represent the next most abundant group. Conserved domain protein transcripts encoded from 14 genes are associated with NADH dehydrogenase I complex. Other highly expressed genes included molecular chaperones, ATP synthase, putative membrane protein, cytochrome c oxidase, GTP-binding protein, putative lipoprotein, translation elongation factor, ABC transporter, and DNA polymerases; all of which represented 0.5-1.7% of the transcriptome.

ECH_0379 mutation caused transcriptional down-regulation of many genes involved in antiporter activity, phage proteins, and those involved in transport and transcription function.

Differential gene expression (DGE) was determined by comparing the RPKM expression values of mutants and wildtype. Fold changes were considered significant with a p-value<0.05, False Discovery Rate (FDR)≤0.001, and consistency of expression values between replicates. The change in gene expression was not significant between wildtype and mutants for housekeeping genes. Based on these criteria, 41 genes were identified as predominantly downregulated and two genes were upregulated in the ECH_0379 gene mutant compared to wildtype (Table 4). The most prominent genes that showed a significant decrease in the transcription levels were those encoding for antiporter proteins, ABC transporters, and ATP-dependent Clp protease (ECH_0367). Four antiporter protein genes: monovalent cation/proton antiporter (ECH_0466), Na(+)/H(+) antiporter subunit C (mrpC) (ECH_0469), potassium uptake protein TrkH (ECH_1093), and nitrogen regulation protein NtrY (ECH_0299) showed a significant decline in the transcript levels. In addition, transcripts for two membrane transporters: cation ABC transporter permease protein transcript of the gene ECH_0517 and another ABC transporter permease protein transcript of the gene ECH_0972 were downregulated. Three genes coding for phage-like proteins {phage prohead protease (ECH_0032), phage portal protein (ECH_0033), and phage major capsid protein (ECH_0830)} were also downregulated in the mutant strain. Transcripts for 6 genes involved in transcription, namely DNA replication and repair protein RecF (ECH_0076), formamidopyrimidine-DNA glycosylase (ECH_0602), dimethyladenosine transferase (ECH_0648), GTP-binding protein EngA (ECH_0504), leucyl-tRNA synthetase (ECH_0794), and endonuclease III (ECH_0857) were also downregulated in this mutant strain. The enzymes of metabolic processes such as glutamate cysteine ligase (GCL) (ECH_0125), DNA/pantothenate metabolism flavoprotein (PMF) (ECH_0374), ATPase, AGF1 (ECH_0392), uroporphyrinogen III synthase (UPGS) (ECH_0480), diaminopimelate decarboxylase (DAPDC) (ECH_0485), biotin-acetyl-CoA-carboxylase ligase (BACL) (ECH_0848), and argininosuccinate lyase (ASL) (ECH_0937) are also down-regulated. Transcripts for 8 hypothetical protein genes; ECH_0021, ECH_0161, ECH_0264, ECH_0289, ECH_0725, ECH_0879, ECH_0913, and ECH_1053 were also among the downregulated genes in this mutant.

TABLE 4

| Gene ID | Wildtype gene expression (RPKM) | ECH_0379 gene expression (RPKM) | Fold change (ECH_0379/Wildtype) FDR ≤0.001, p-value <0.05 | Gene name |
|---|---|---|---|---|
| Down regulated genes | | | | |
| ECH_0021 | 391 | 211 | −1.88 | conserved hypothetical protein |
| ECH_0032 | 82 | 26 | −3.2 | phage prohead protease, HK97 family |
| ECH_0033 | 41 | 20 | −1.53 | phage portal protein, HK97 family |
| ECH_0076 | 287 | 59 | −5 | putative DNA replication and repair protein RecF |
| ECH_0125 | 386 | 185 | −2.08 | glutamate-cysteine ligase |
| ECH_0161 | 81 | 42 | −1.92 | hypothetical protein |
| ECH_0188 | 586 | 121 | −5 | putative surface protein |
| ECH_0264 | 814 | 194 | −4.16 | conserved hypothetical protein |
| ECH_0289 | 102 | 52 | −1.96 | hypothetical protein |
| ECH_0299 | 1432 | 442 | −1.81 | putative nitrogen regulation protein NtrY |
| ECH_0367 | 3407 | 1784 | −1.92 | ATP-dependent Clp protease, ATP-binding subunit ClpB |
| ECH_0374 | 411 | 157 | −2.63 | DNA/pantothenate metabolism flavoprotein family protein |
| ECH_0392 | 845 | 159 | −5.55 | ATPase, AFG1 family |
| ECH_0466 | 432 | 252 | −1.72 | monovalent cation/proton antiporter |
| ECH_0469 | 137 | 52 | −5.55 | Na(+)/H(+) antiporter subunit C |
| ECH_0473 | 793 | 306 | −5.55 | aromatic-rich protein family |
| ECH_0480 | 319 | 92 | −3.22 | uroporphyrinogen-III synthase |
| ECH_0485 | 537 | 172 | −3.14 | diaminopimelate decarboxylase |
| ECH_0504 | 859 | 288 | −3.03 | GTP-binding protein EngA |
| ECH_0517 | 503 | 52 | −10 | putative cation ABC transporter, permease protein |
| ECH_0523 | 1525 | 159 | −10 | conserved domain protein |
| ECH_0541 | 251 | 124 | −2 | 5-formyltetrahydrofolate cyclo-ligase family protein |
| ECH_0602 | 84 | 24 | −3.57 | formamidopyrimidine-DNA glycosylase |
| ECH_0648 | 399 | 138 | −2.94 | dimethyladenosine transferase |
| ECH_0725 | 648 | 280 | −2.32 | conserved hypothetical protein |
| ECH_0756 | 815 | 153 | −5.55 | divalent ion tolerance protein CutA1 |
| ECH_0789 | 1154 | 363 | −3.22 | cytochrome c-type biogenesis protein CcmE |
| ECH_0794 | 1593 | 306 | −5.26 | leucyl-tRNA synthetase |
| ECH_0830 | 397 | 123 | −3.22 | phage major capsid protein, HK97 family |
| ECH_0848 | 1015 | 253 | −4 | biotin—acetyl-CoA-carboxylase ligase |
| ECH_0857 | 638 | 311 | −2.04 | endonuclease III |
| ECH_0864 | 455 | 246 | −1.85 | conserved domain protein |
| ECH_0879 | 520 | 153 | −3.44 | hypothetical protein |
| ECH_0913 | 570 | 114 | −5 | conserved hypothetical protein |
| ECH_0937 | 521 | 284 | −1.85 | argininosuccinate lyase |
| ECH_0972 | 524 | 285 | −1.85 | ABC transporter, permease protein |
| ECH_0998 | 722 | 332 | −2.17 | ubiquinone/menaquinone biosynthesis methlytransferase UbiE |
| ECH_1053 | 541 | 248 | −2.22 | conserved hypothetical protein |
| ECH_1063 | 201 | 106 | −1.92 | modification methylase, HemK family |
| ECH_1081 | 310 | 78 | −4 | SURF1 family protein |
| ECH_1084 | 684 | 364 | −1.88 | AraM protein |
| ECH_1093 | 973 | 320 | −2.32 | putative potassium uptake protein TrkH |
| ECH_1101 | 1143 | 190 | −6.25 | prolipoprotein diacylglyceryl transferase |

TABLE 4-continued

| Gene ID | Wildtype gene expression (RPKM) | ECH_0379 gene expression (RPKM) | Fold change (ECH_0379/Wildtype) FDR ≤0.001, p-value <0.05 | Gene name |
|---|---|---|---|---|
| Up regulated genes | | | | |
| ECH_0684 | 1765 | 3651 | 2.06 | ankyrin repeat protein |
| ECH_0495 | 942 | 1492 | 1.58 | type IV secretion system protein VirB4 |

Differential Transcriptional Regulation of T4SS and p-28 OMP Gene Cluster Genes in Mutant ECH_0490

In the ECH_0490 mutant strain, 37 genes were significantly downregulated and 17 genes were up-regulated (Table 5). Four of the downregulated genes belonged to the T4SS are ECH_0494 (VirB3), ECH_0496 (VirB6), ECH_0498 (VirB6), and ECH_0499 (VirB6); and a type I secretion membrane fusion protein (T1SS_HlyD) (ECH_0970). Molecular chaperone genes, such as a cold shock protein (CSP) (ECH_0298) and ATP-dependent Clp protease, and a ATP-binding subunit ClpA (ClpA) were also downregulated. The transport proteins including the protein export membrane protein (SecF) (ECH_0095), preprotein translocase (SecY) (ECH_0428), potassium uptake protein (TrkH) (ECH_1093), and nitrogen regulation protein (NtrY) (ECH_0299) were also among the downregulated genes. Metabolic enzymes involved in biosynthetic processes, {tetrahydropyridine-2-carboxylate N-succinyltransferasem (dapD) (ECH_0058), quinone oxidoreductase (ECH_0385), metalloendopeptidase, (MEP) (ECH_0644), peptide deformylase (PDF) (ECH_0939), serine/threonine phosphatase (PSP) (ECH_0964), pyrophosphatase (PPi) (ECH_1014), and orotate phosphoribosyltransferase (OPRTase) (ECH_1108)}, were also down-regulated. Transcription- and translation-related genes, such as elongation factors (EF-Tu) (ECH_0515), aminoacyl-tRNA synthetases (IARS) (ECH_0538), DNA-binding protein (HU) (ECH_0804), 3'-5' exonuclease domain (ECH_1011), and DNA-binding response regulator (ECH_1012), were also downregulated.

TABLE 5

| Gene ID | Wildtype gene expression (RPKM) | ECH_0490 gene expression (RPKM) | Fold change (ECH_0490/wildtype) FDR ≤0.001, p-value <0.05 | Gene name |
|---|---|---|---|---|
| Down regulated genes | | | | |
| ECH_0058 | 1902 | 1006 | −1.88 | 2,3,4,5-tetrahydropyridine-2-carboxylate N-succinyltransferase |
| ECH_0085 | 1119 | 523 | −2.17 | ABC transporter, ATP-binding protein |
| ECH_0095 | 1921 | 990 | −1.96 | protein export membrane protein SecF |
| ECH_0264 | 814 | 310 | −5.55 | conserved hypothetical protein |
| ECH_0298 | 8295 | 3870 | −2.17 | cold shock protein, CSD family; |
| ECH_0299 | 719 | 314 | −2.17 | putative nitrogen regulation protein NtrY |
| ECH_0300 | 557 | 283 | −2 | putative ribonuclease D |
| ECH_0385 | 1659 | 663 | −2.5 | quinone oxidoreductase |
| ECH_0428 | 979 | 425 | −2.32 | preprotein translocase, SecY subunit |
| ECH_0470 | 1220 | 598 | −2 | ribonuclease, Rne/Rng family |
| ECH_0475 | 977 | 444 | −2.22 | signal recognition particle protein |
| ECH_0483 | 158 | 77 | −2.04 | primosomal protein N |
| ECH_0494 | 2326 | 1034 | −2.17 | type IV secretion system protein VirB3 |
| ECH_0496 | 1059 | 435 | −2.43 | type IV secretion system protein VirB6 |
| ECH_0498 | 1154 | 490 | −2.38 | type IV secretion system protein,VirB6 family |
| ECH_0499 | 1129 | 558 | −2 | type IV secretion system protein,VirB6 family |
| ECH_0515 | 1968 | 910 | −2.17 | translation elongation factor Ts |
| ECH_0525 | 1055 | 427 | −2.5 | conserved domain protein |
| ECH_0538 | 729 | 355 | −2.08 | isoleucyl-tRNA synthetase |
| ECH_0567 | 626 | 177 | −3.57 | ATP-dependent Clp protease, ATP-binding subunit ClpA |
| ECH_0585 | 475 | 229 | −2.08 | conserved domain protein |
| ECH_0644 | 1902 | 764 | −2.5 | putative metalloendopeptidase, glycoprotease family |
| ECH_0700 | 2670 | 1073 | −2.5 | hypothetical protein |

TABLE 5-continued

| Gene ID | Wildtype gene expression (RPKM) | ECH_0490 gene expression (RPKM) | Fold change (ECH_0490/wildtype) FDR ≤0.001, p-value <0.05 | Gene name |
|---|---|---|---|---|
| ECH_0804 | 3113 | 1292 | −2.43 | DNA-binding protein HU |
| ECH_0820 | 409 | 167 | −2.5 | conserved hypothetical protein |
| ECH_0840 | 935 | 296 | −3.22 | 2-polyprenylphenol 6-hydroxylase |
| ECH_0939 | 752 | 276 | −2.77 | putative polypeptide deformylase |
| ECH_0953 | 2914 | 1480 | −2 | ribosomal protein L7/L12 |
| ECH_0964 | 1281 | 557 | −2.32 | serine/threonine phosphoprotein phosphatase |
| ECH_0970 | 474 | 247 | −1.92 | type I secretion membrane fusion protein, HlyD family |
| ECH_1011 | 2253 | 1104 | −2.04 | 3'-5' exonuclease family protein |
| ECH_1012 | 3353 | 1605 | −2.08 | DNA-binding response regulator |
| ECH_1014 | 1661 | 536 | −3.12 | inorganic pyrophosphatase |
| ECH_1093 | 973 | 416 | −2.38 | putative potassium uptake protein TrkH |
| ECH_1108 | 1903 | 938 | −2.04 | orotate phosphoribosyltransferase |
| ECH_1139 | 545 | 285 | −1.92 | major outer membrane protein OMP-1D |
| Up-regulated genes | | | | |
| ECH_0009 | 7047 | 16828 | 2.38 | putative membrane protein |
| ECH_0039 | 316 | 931 | 2.94 | 120 kDa immunodominant surface protein |
| ECH_0166 | 42488 | 96364 | 2.26 | conserved hypothetical protein |
| ECH_0167 | 718 | 2654 | 3.70 | tryptophanyl-tRNA synthetase |
| ECH_0169 | 161 | 397 | 2.46 | riboflavin biosynthesis protein RibD |
| ECH_0230 | 991 | 4109 | 4.15 | putative membrane protein |
| ECH_0251 | 1042 | 2185 | 2.1 | hypothetical protein |
| ECH_0303 | 1018 | 2856 | 2.80 | BolA family protein |
| ECH_0367 | 849 | 1274 | 2.49 | ATP-dependent Clp protease, ATP-binding subunit ClpB |
| ECH_0450 | 1261 | 3710 | 2.94 | conserved hypothetical protein |
| ECH_0531 | 1363 | 11788 | 8.65 | hypothetical protein |
| ECH_0630 | 732 | 1688 | 2.30 | FeS cluster assembly scaffold IscU |
| ECH_0655 | 1840 | 2763 | 2.03 | RNA polymerase sigma-32 factor |
| ECH_0753 | 1932 | 4153 | 2.15 | conserved hypothetical protein |
| ECH_0818 | 374 | 1222 | 3.26 | major facilitator family transporter |
| ECH_0878 | 217 | 1126 | 5.17 | hypothetical protein |
| ECH_1121 | 1578 | 3132 | 3.1 | major outer membrane protein Omp-1N |
| ECH_1136 | 698 | 8270 | 2.37 | major outer membrane protein OMP-1B |
| ECH_1143 | 3957 | 8359 | 2.24 | major outer membrane protein P28 |
| ECH_1146 | 190 | 1100 | 6.73 | major outer membrane protein P28-2 |

Upregulated protein genes in this mutant included 7 that belonged to the transmembrane protein category. Of these, four belonged to the p-28 OMP gene cluster {ECH_1143 (OMP-p28), ECH_1146 (OMP-p28-2), ECH_1136 (OMP-1B), and ECH_1121 (OMP-1N)}. In addition, two putative membrane protein genes (ECH_0009, ECH_0230) and an immunodominant surface protein gene (ECH_0039) were upregulated. Transcripts for the heat shock proteins ATP-dependent Clp protease, ClpA (ECH_0567) and ATP-binding chaperon, ClpB (ECH_0367), and the stress response-associated RNA polymerase sigma factor (RpoH) (ECH_0655) were also upregulated. Transcripts for two genes coding for iron sulfur proteins {BolA family protein (ECH_0303) and FeS cluster assembly scaffold (IscU) (ECH_0630)} were similarly up-regulated. We observed differential expression of six hypothetical protein genes, which included ECH_0166, ECH_0251, ECH_0450, ECH_0531, ECH_0753, and ECH_0878.

Mutation in ECH_0660 gene led to minimal transcriptional alterations

While we observed drastic gene expression changes in both ECH_0379 and ECH_0490 mutants, ECH_0660 mutant transcriptome showed minimal variations compared to wildtype; we observed only five genes as notably differentially expressed in this mutant (Table 6). The genes included nitrogen regulation protein (NtrY) (ECH_0299) and the ABC transporter permease protein (ECH_0972) as down-regulated genes, whereas the heme exporter protein CcmA (ECH_0295) and chaperonin (ECH_0364) were upregulated. We also identified several commonly differentially-expressed genes in ECH_0379 and ECH_0490 (Table 7). The ribonuclease D (ECH_0300) and potassium uptake protein (ECH_1093) were commonly down regulated in ECH_0379 and ECH_0490. T4SS protein VirB4 gene was down-regulated in ECH_0490 mutant, whereas this gene was up-regulated in ECH_0379 mutant. Contrary to this, ClpB was down-regulated in ECH_0379 mutant and upregulated in ECH_0490 mutant.

TABLE 6

| Gene ID | Wildtype gene expression (RPKM) | ECH_0660 gene expression (RPKM) | Fold change (ECH_0660/Wildtype) FDR ≤0.001, p-value <0.05 | Gene name |
|---|---|---|---|---|
| Down regulated genes | | | | |
| ECH_0299 | 1432 | 720 | −2 | putative nitrogen regulation protein NtrY |
| ECH_0972 | 524 | 309 | −1.69 | ABC transporter, permease protein |
| Up regulated genes | | | | |
| ECH_0295 | 336 | 631 | 1.87 | putative heme exporter protein CcmA |
| ECH_0364 | 6801 | 12150 | 1.78 | chaperonin, 10 kDa conserved |
| ECH_1147 | 1982 | 4756 | 2.39 | hypothetical protein |

TABLE 7

| Gene ID | Wildtype gene expression (RPKM) | Mutant gene expression (RPKM) | Fold change FDR ≤0.001, p-value <0.05 | Gene name | mutants |
|---|---|---|---|---|---|
| Down regulated genes | | | | | |
| ECH_0299 | 1432 | 442 | −1.81 | putative nitrogen regulation protein NtrY | ECH_0379 ECH_0490 |
| ECH_0264 | 814 | 310 | −2.63 | conserved hypothetical protein | ECH_0379 ECH_0490 |
| ECH_0300 | 557 | 283 | −2 | putative ribonuclease D | ECH_0379 ECH_0490 |
| ECH_0864 | 279 | 193 | −1.44 | conserved domain protein | ECH_0379 ECH_0490 |
| ECH_1093 | 972 | 416 | −1.81 | putative potassium uptake protein TrkH | ECH_0379 ECH_0490 |
| ECH_0495 | 833 | 517 | −1.63 | type IV secretion system protein VirB4 | ECH_0490 |
| ECH_0367 | 3407 | 1783 | −1.92 | ATP-dependent Clp protease, ATP-binding subunit ClpB | ECH_0379 |
| ECH_0745 | 712 | 437 | −1.63 | conserved domain protein | ECH_0379 |
| Up regulated | | | | | |
| ECH_0495 | 942 | 1492 | 1.58 | type IV secretion system protein VirB4 | ECH_0379 |
| ECH_0367 | 849 | 1275 | 2.49 | ATP-dependent Clp protease, ATP-binding subunit ClpB | ECH_0490 |
| ECH_0745 | 547 | 920 | 1.68 | conserved domain protein | ECH_0490 |

Validation of RNA Seq Data by Quantitative Real-Time Reverse Transcription PCR

Quantitative real-time quantitative reverse transcriptase-PCR (qRT-PCR) analysis was carried out on thirteen randomly selected genes identified as differentially transcribed according to the RNA seq data. To generate qRT-PCR data, we first normalized RNA samples to a constitutively expressed E. chaffeensis gene coding for the 16S RNA as previously described in Cheng et al. Transcript abundance for 7 down-regulated genes in ECH_379 mutant, including ECH_0466 and mrpC, ClpB, ECH_0033, NtrY, TrkH, and ECH_0972 were validated. Similarly, 6 upregulated genes from ECH_0490 mutant strain, including four transcripts belonging to an OMP gene cluster (OMP-p28, OMP-1B, OMP-1N, OMP-p28-2) and one each from ClpB and RpoH genes were verified by qRT-PCR. Likewise, the down-regulation of transcripts for the ECH_0299 and ECH_0972 genes were confirmed in ECH_0660 mutant by qRT-PCR.

Discussion

Isolation of cell-free bacterial RNA from highly abundant host RNA is the first challenge in transcriptional profiling of intracellular pathogens. Rickettsiales require culturing in host cells and then need to be purified before extracting RNA for transcriptome evaluation experiments. To document the impact of three transposon mutations on E. chaffeensis transcription, we first developed a method for isolation and purification of host cell-free E. chaffeensis organisms, from which we isolated RNA and then subjected to next generation sequencing (NGS) analysis. To isolate cell-free E. chaffeensis, we started with an efficient host cell lysis protocol, and then filtration of whole cell lysate, followed by a renografin density gradient centrifugation. The second challenge was to obtain host cell-free RNA for transcriptome profiling. Previous studies report that bacterial RNA enrichment methods result in the enrichment of bacterial RNA reads only 3-10%. Isolation of host cell-free bacteria and the bacterial RNA purification steps implemented in our study allowed a greater enrichment of E. chaffeensis RNA. In our current studies, we were able to enrich the bacterial RNA, which helped in generating up to 19% high mapping RNA reads. Notably, deep RNA sequencing analysis aided in mapping 80% of E. chaffeensis genes expressed in infected macrophage host cells.

Among the highly expressed genes, the p28-OMP multigene cluster was dominant in the transcriptome. The E. chaffeensis p28-OMP multigene locus contains 22 tandemly arranged genes coding for the bacterial immunodominant proteins. The presence of all 22 transcripts in the RNA seq data suggest that the gene cluster is among the most abundantly expressed genes. These observations are consistent with our previous proteomic study where we reported the p28-OMP genes' expression abundance. NADH dehydrogenase I complex genes were also highly expressed in *E. chaffeensis*. NADH dehydrogenase counters the phagosomal NOX2 response to inhibit host cell apoptosis34. T4SS effector proteins in some pathogenic bacteria are considered as important in manipulating a host gene expression to undermine the host immune response. The contributions of T4SS effectors in pathogenicity are already reported for rickettsiales, including for *A. marginale, A. phagocytophilum, E. canis*, and *E. chaffeensis*. The RNA seq analysis identified several transcripts encoding for T4SS proteins, including VirB3, B4, B6, B8, B9, B10, and B11. Chaperone protein genes DnaK, DnaJ, GroE, and ClpB were also highly expressed in both wildtype and mutant strains. The presence of such proteins involved in cell homeostasis and the oxidative stress response is reported in other rickettsiales, suggesting that their gene products are also critical for the *E. chaffeensis* stress response if the pathogen proteome is similarly altered as per the transcriptome reported in the current study. Indeed, our recent study suggests that the stress response proteins are important for *E. chaffeensis*. Other highly expressed protein genes included those encoding for housekeeping ribosomal proteins involved in protein synthesis, putative membrane proteins, ABC transporter, and lipoprotein; all of which are likely important for the pathogen's protein synthesis, transport, trafficking, and effector secretion into the host cells. ATP synthase subunit, cytochrome c oxidase, DNA polymerases, GTP-binding protein and translation elongation factors involved energy metabolism, cell division, and transcriptional regulation were also among the highly expressed genes in both wildtype and mutant organisms. The extent of transcriptome coverage is higher than the previously reported for *E. chaffeensis* in ISE6 and AAE2 tick cells8. This is substantial for both the enhanced detection of intracellular pathogen transcripts and also because of the abundance of gene expressions observed. Higher coverage of the transcriptome likely resulted from deep sequencing of the RNAs by next-generation sequencing compared to microarray analysis. This global set of highly expressed genes may represent products involved in pathogenicity, replication and survival of *E. chaffeensis* in host cell environment. Four transcripts that code for ankyrin repeat proteins, which are shown to mediate protein-protein interactions, were also identified in the transcriptome. Notably, the transcriptome from the wildtype and mutant organisms contained 216 transcripts that code for hypothetical proteins with unknown function. As these were within the core transcriptome, we anticipate that they represent an important set of transcribed genes for *E. chaffeensis* replication.

Transcription from large numbers of genes in ECH_0379 mutant was found to be reduced compared to wildtype. Genes representing antiporters, ABC transporters, chaperons, metabolic enzymes, and transcription regulators are among the down-regulated genes (Table 4). We predict that the mutation in the anti-porter protein gene caused a metabolic depression. Antiporter and transport proteins play an important role in the transport of ions and solutes across the cell membranes of bacteria. Antiporters are integral membrane proteins that perform secondary transport of Na+ and/or K+ for H+ across a phospholipid membrane. The *E. chaffeensis* genome contains several genes having homology to antiporter proteins or their subunits, suggesting that they are needed for the pathogen's intraphagosomal replication and survival in a host. In particular, antiporters aid bacteria in maintaining pH, salt, and temperature conditions. We observed a significant decline in transcription of antiporter genes such as monovalent cation/H+ antiporter subunit C (ECH_0469) and ECH_0466. Disrupting the antiporter function or preventing their expression may affect the pathogen's growth in vivo. Indeed, mutation in the ECH_0379 gene resulted in the attenuated growth of the organism in both an incidental host (dog) and in the reservoir host (white-tailed deer). ABC transporters also are involved in uptake of ions and amino acids and may play an important role in a pathogen's ability to infect and survive in a host cell environment. The ECH_0379 mutant had low levels of transcriptional activity of the genes ECH_0517 and ECH_0972 encoding for ABC transporters, which function at different stages in the pathogenesis of infection. These proteins promote the survival of pathogens in the host microenvironments. The mutation possibly interferes with transport mechanisms, thereby affecting its ability to infect and survive in host cells. The mutation may have also caused alterations to the transcriptions of genes involved in physiological responses, such as regulating the pathogen's metabolic activities. We also found down-regulation of several transcripts encoding for metabolic enzymes: glutamate-cysteine ligase, DNA/pantothenate metabolism flavoprotein family protein, ATPase, uroporphyrinogen-III synthase, diaminopimelate decarboxylase, biotin-acetyl-CoA-carboxylase ligase, and argininosuccinate lyase. In general, a pathogen's survival in an intracellular environment depends on its ability to derive nutrients from the host cell. Pathogenic bacteria use metabolic pathways and virulence-associated factors that undermine the host immune system so that they can derive nutrients from their host cells. It is possible that the downregulation of the transcripts from the aforementioned genes in the ECH_0379 mutant hampers the bacterial metabolic response and its capacity to derive nutrients from the host. The mutation also caused decreased expression of genes encoding DNA replication and repair protein, formamidopyrimidine-DNA glycosylase, dimethyladenosine transferase, and leucyl-tRNA synthetase. This may have also contributed to defects in pathogen's intracellular growth and survival. Our prior studies suggest that despite the mutant's attenuated growth, it failed to offer complete protection against wildtype infection challenge. If the changes in the transcriptome correlate with changes in the proteome, variations in the mutant organisms' protein expression relative to the wildtype *E. chaffeensis* may result in an altered host response, thus making the host less effective in initiating a protective host response when exposed to the mutant organisms.

Pathogenic bacteria produce T4SS effectors to weaken the host cell gene expression and contributes to bacterial virulence. RNA seq data suggested declined expressions of various T4SS component protein gene transcripts in ECH_0490 mutant. We also observed decreased transcription of chaperone proteins and several genes involved in the transcription and translational machinery, and exonuclease and DNA-binding regulator gene transcripts in the ECH_0490 mutant strain. On the contrary, ClpB (a major stress response heat shock protein) and RpoH (stress response RNA polymerase transcriptional subunit) showed increased transcription in the mutant.

Chaperone proteins play a key role in protein disaggregation and in aiding the pathogen to overcome the likely host cell-induced stress. ClpB reactivates aggregated proteins accumulating under stress conditions and it was abundantly expressed during replication stage of *E. chaffeensis*. Preventing or reducing protein aggregation and the associated protein inactivation during the bacterial growth within a host cell may benefit the pathogen in enhancing its survival. The RNA polymerase transcription regulator, RpoH, is also important for the pathogen's continued growth as it aids in promoting the expression of stress response proteins. Consistent with the prediction, increased expression of ClpB and RpoH was observed in the current study for ECH_0490 mutant. The enhanced expression from these two important genes likely enables the mutant to grow similarly to wildtype *E. chaffeensis* in vertebrate and tick hosts, as reported in our previous studies. Outer membrane proteins perform a variety of functions such as invasion, transport, immune response, and adhesion that are vital to the survival of *Ehrlichia* species, including *E. chaffeensis* and *E. ruminantium* in a host. The ECH_0490 mutant had increased abundance of OMPs compared to wildtype organisms. We found seven transmembrane genes coding for immunodominant P28/OMP family of proteins (OMP_p28, OMP_p28-2, OMP-1B, and OMP-1N) and membrane proteins (ECH_0039, ECH_0009, and ECH_0230) to be upregulated. Significant changes in the abundance of the outer membrane proteins may be associated with overall changes in the membrane architecture, thereby altering the pathogen's susceptibility to host defense. The transcriptional changes noted in the ECH_0490 mutant may not have had any negative impact on the pathogen, as the mutant grows similar to the wildtype pathogen both in white-tailed deer (the reservoir host) and in dogs (an incidental host), and in its tick host, *Amblyomma americanum*. Transcriptional activity assessment of the genes ECH_0490 (lipoic acid synthetase) and ECH_0492 (putative phosphate ABC transporter), both of which are located up and down stream to the transposon insertion mutation, respectively, suggested that the mutation has no effect on these genes' transcription. The diverse changes in the transcriptome of the mutant, while having no impact near the mutation site, suggest that the mutation impacted global gene expression and yet did not adversely affect the pathogen's survival in vertebrate and tick hosts.

The most notable observation was the apparent minimal variation in the transcriptome of the ECH_0660 mutant compared to the wildtype *E. chaffeensis*. Importantly, mutation within ECH_0660 gene causes severe growth defects in vivo in vertebrate hosts. Further, infection with this mutant also initiates a strong host response and confers protection against wildtype pathogen infection challenge. In the current study, we observed only minor changes in the gene expression in this mutant compared to wildtype. The minor changes in gene expression included genes encoding for putative nitrogen regulation protein, ABC transporter, heme exporter protein and GroES, but the variations were significantly less compared to numerous changes described in the previous two mutants. Together, these data suggest that the mutation in ECH_0660 gene led to fewer transcriptional alterations. Assuming that the proteomes of the wild type and mutant strains of *E. chaffeensis* are similarly altered as the transcriptomes, then ECH_0660 mutant proteome may be very similar to the wildtype bacterium. The greater degree of similarity between this mutant and the wildtype may enable the vertebrate hosts to recognize this mutant as closer to wildtype organism, thus inducing a stronger host response that mimics wildtype infection. The replication defect reported earlier with this mutant may have resulted due to the loss of gene expression from fewer genes such as ECH_0659 and ECH_0660, while maintaining most of the transcriptome similar to the wildtype.

CONCLUSIONS

RNA deep sequencing studies in intracellular bacteria are still a major challenge. The RNA seq data reported here provide the first snapshot of comparative transcriptomics of *E. chaffeensis*. Sequencing of enriched bacterial RNA from wildtype and mutant strains yielded a high coverage of genes. A mutation in the ORF of ECH_0379 gene caused drastic down-regulation of genes leading to metabolic depression, which may have contributed to the mutant's attenuation in vertebrate hosts. While a mutation downstream to the protein coding sequence of ECH_0490 gene induced global changes in gene expression, up regulation of stress response regulatory genes may have helped the mutant survive in the vertebrate hosts and tick hosts. A mutation within ECH_0660 gene coding sequence resulted in few transcriptional changes, thus keeping the integrity of its transcriptome similar to wildtype. While the transcriptome data are suggestive of protein expression variations, additional experimental validation from protein analysis studies is necessary to confirm the results. Together, this study offers the first detailed description of transcriptome data for *E. chaffeensis*, suggesting that variations observed in the pathogen's ability to survive in a host and the host's ability to induce protection against the pathogen may be the result of global changes in the gene expression, which in turn may impact changes in the pathogen's proteome.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11541108B2). An electronic copy of the "Sequence Listing" will also be available from the USPTO upon request and payment of the fee set forth in 37 CFR 1.19(b)(3).

What is claimed is:

1. An immunogenic composition comprising:
   a Rickettsiale bacteria having a targeted allelic exchange mutation therein, wherein said targeted allelic exchange mutation comprises a disrupted gene that has had the integrity thereof restored; and
   a component selected from the group consisting of a veterinary-acceptable carrier, a pharmaceutical-acceptable carrier, an adjuvant, a preservative, a buffer, an antibiotic, cell culture supernatant, an immunomodulatory agent, and any combination thereof.

2. The immunogenic composition of claim 1, wherein said Rickettsiale bacteria is selected from the group consisting of species of *Ehrlichia, Anaplasma, Neorickettsia, Rickettsia,* and *Orientia.*

3. The immunogenic composition of claim 2, wherein the *Ehrlichia* bacteria species is selected from the group consisting of *Ehrlichia chaffeensis, Ehrlichia ruminatium,* and *Ehrlichia canis.*

4. The immunogenic composition of claim 2, wherein the *Anaplasma* bacteria is selected from the group consisting of *Anaplasma phagocytophilum, Anaplasma platys,* and *Anaplasma marginale.*

5. The immunogenic composition of claim 1, wherein the targeted allelic mutation attenuates the bacteria and/or inactivates a gene.

6. The immunogenic composition of claim 5, wherein the gene functions as an aid to replication.

7. The immunogenic composition of claim 2, wherein the targeted allelic exchange mutation is in a location selected from the group consisting of:
   a) Ech_0379 or Ech_0660 in *Ehrlichia chaffeensis;*
   b) Ecaj_0381 in *Ehrlichia canis;*
   c) APH_0634 in *Anaplasma phagocytophilum*
   d) Erum_3930 in *E. ruminatium;*
   e) AMH_581 in *Anaplasma marginale;* or
   f) EMUR_02070 in *Ehrlichia muris* AS145.

8. The immunogenic composition of claim 1, wherein said component is an adjuvant selected from the group consisting of a saponin, a cyclic GMP-AMP, montanide gel, or any combination thereof.

9. The immunogenic composition of claim 1, further comprising an antigen from another disease causing organism.

10. The immunogenic composition of claim 1, wherein said bacteria includes a sequence with at least 70% sequence identity with SEQ ID NO. 35, 54, or 55.

11. An immunogenic composition comprising:
    a Rickettsiale or Chlamydiale bacteria having a targeted allelic exchange mutation therein and includes a sequence with at least 70% sequence identity with SEQ ID NO. 35, 54, or 55; and
    a component selected from the group consisting of a veterinary-acceptable carrier, a pharmaceutical-acceptable carrier, an adjuvant, a preservative, a buffer, an antibiotic, cell culture supernatant, an immunomodulatory agent, and any combination thereof.

12. A method of reducing the incidence of or severity of at least one clinical sign caused by a Rickettsiale bacteria comprising the step of:
    administering an immunogenic composition at least once to an animal in need thereof, wherein said immunogenic composition comprises a Rickettsiale bacteria having a targeted allelic exchange mutation therein, wherein said targeted allelic exchange mutation comprises a disrupted gene that has had the integrity thereof restored, and a component selected from the group consisting of a veterinary-acceptable carrier, a pharmaceutical-acceptable carrier, an adjuvant, a preservative, a buffer, a stabilizer, an antibiotic, cell culture supernatant, an immunomodulatory agent, and any combination thereof.

13. The method of claim 12, wherein said immunogenic composition is administered using an administration mode selected from the group consisting of intravenously, intramuscularly, intranasally, intradermally, intratracheally, intravaginally, intravenously, intravascularly, intraarterially, intraperitoneally, orally, intrathecally, by direct injection into any target tissue, or any combination thereof.

14. The method of claim 12, wherein said reduction in incidence is at least 10% and is in comparison to a group of animals that have not received an administration of the immunogenic composition.

15. The method of claim 12, wherein said reduction in severity is at least 10% in comparison to a group of animals that have not received an administration of the immunogenic composition.

16. The method of claim 12, wherein the Rickettsiale bacteria is selected from the group consisting of species of *Ehrlichia, Anaplasma, Neorickettsia, Rickettsia,* and *Orientia.*

17. The method of claim 16, wherein the *Ehrlichia* bacteria is selected from the group consisting of *Ehrlichia chaffeensis, Ehrlichia ruminatium,* and *Ehrlichia canis.*

18. The method of claim 16, wherein the Anaplasma bacteria is selected from the group consisting of *Anaplasma phagocytophium, Anaplasma platys,* and *Anaplasma marginale.*

19. The method of claim 12, wherein the targeted allelic exchange mutation inactivates a gene.

20. The method of claim 12, wherein the targeted allelic exchange mutation is in a location selected from the group consisting of:
    a) Ech_0379, or Ech_0660 in *Ehrlichia chaffeensis;*
    b) Ecaj_0381 in *Ehrilichia canis;*
    c). APH_0634 in *Anaplasma phagocytophilum;*
    d) Erum_3930 in *E. ruminatium;*
    e) AMH_581 in *Anaplasma marginale;* or
    f) EMUR_02070 in *Ehrlichia muris* AS145.

21. The method of claim 12, wherein said bacteria includes a sequence with at least 70% sequence identity with SEQ ID NO. 35, 54, or 55.

22. The method of claim 12, wherein said animal is selected from the group consisting of pigs, cattle, goats, horses, dogs, deer, coyote, cats, and poultry.

23. The method of claim 12, wherein said animal is between 3 weeks and 6 months of age when receiving said administration.

* * * * *